US009345866B2

(12) United States Patent
Kubo et al.

(10) Patent No.: US 9,345,866 B2
(45) Date of Patent: May 24, 2016

(54) NASAL CAVITY ADMINISTRATION CONTAINER

(75) Inventors: Tomohiko Kubo, Osaka (JP); Teruhisa Hirobe, Osaka (JP)

(73) Assignee: NIPRO CORPORATION, Osaka (JP)

( * ) Notice: Subject to any disclaimer, the term of this patent is extended or adjusted under 35 U.S.C. 154(b) by 95 days.

(21) Appl. No.: 14/117,319

(22) PCT Filed: May 11, 2012

(86) PCT No.: PCT/JP2012/062211
§ 371 (c)(1),
(2), (4) Date: Nov. 12, 2013

(87) PCT Pub. No.: WO2012/157582
PCT Pub. Date: Nov. 22, 2012

(65) Prior Publication Data
US 2014/0303565 A1    Oct. 9, 2014

(30) Foreign Application Priority Data

May 13, 2011    (JP) ................................. 2011-108640

(51) Int. Cl.
*A61M 31/00*    (2006.01)
*A61M 15/08*    (2006.01)
*A61M 3/00*    (2006.01)
(Continued)

(52) U.S. Cl.
CPC ................. *A61M 31/00* (2013.01); *A61M 3/00* (2013.01); *A61M 5/3158* (2013.01); *A61M 5/31511* (2013.01); *A61M 11/007* (2014.02); *A61M 15/08* (2013.01); *A61M 3/0262* (2013.01); *A61M 5/31505* (2013.01);
(Continued)

(58) Field of Classification Search
CPC ............ B05B 11/025; A61M 5/31591; A61M 5/31555; A61M 5/3156; A61M 5/31563; A61M 5/31505; A61M 5/31548
See application file for complete search history.

(56) References Cited

U.S. PATENT DOCUMENTS 2,648,334 A * 8/1953 Brown et al. .................. 604/205
4,073,321 A * 2/1978 Moskowitz ..................... 141/27
(Continued)

FOREIGN PATENT DOCUMENTS

EP    0 904 792 A2    3/1999
JP    6-13054 B2    2/1994
(Continued)

OTHER PUBLICATIONS

Japanese Notice of Allowance, dated Nov. 17, 2015, for Japanese Application No. 2013-515135, as well as an English translation.

*Primary Examiner* — Aarti B Berdichevsky
(74) *Attorney, Agent, or Firm* — Birch, Stewart, Kolasch & Birch, LLP

(57) ABSTRACT

A nasal cavity administration container includes a body section including a medical fluid storage section having an opening and a plunger having a pressing part, and a plunger moving amount regulation member having a stopper and being engaged with the body section, an engagement with the body section being relieved only in a state where the pressing part abuts on the stopper. When the plunger is pushed into the medical fluid storage section, the plunger moves forward until the pressing part abuts on the stopper. The plunger is further pushed into the medical fluid storage section with the plunger moving amount regulation member detached from the body section. The nasal cavity administration container can administer a medical fluid easily and appropriately.

6 Claims, 33 Drawing Sheets

(51) Int. Cl.
*A61M 5/315* (2006.01)
*A61M 11/00* (2006.01)
*A61M 3/02* (2006.01)

(52) U.S. Cl.
CPC ............... *A61M 2005/31516* (2013.01); *A61M 2005/31518* (2013.01); *A61M 2210/0618* (2013.01)

(56) References Cited

U.S. PATENT DOCUMENTS

| | | | |
|---|---|---|---|
| 4,444,335 A | 4/1984 | Wood et al. | |
| 4,654,035 A * | 3/1987 | Ando | 604/210 |
| 4,874,385 A * | 10/1989 | Moran et al. | 604/208 |
| 5,009,645 A | 4/1991 | Silver et al. | |
| 5,328,486 A * | 7/1994 | Woodruff | 604/208 |
| 5,601,077 A | 2/1997 | Imbert | |
| 5,662,098 A | 9/1997 | Yoshida | |
| 5,700,247 A * | 12/1997 | Grimard et al. | 604/220 |
| 5,951,526 A * | 9/1999 | Korisch et al. | 604/208 |
| 5,975,355 A * | 11/1999 | Cecala et al. | 222/43 |
| 6,789,750 B1 | 9/2004 | Heldt | |
| 7,296,566 B2 | 11/2007 | Alchas | |
| 7,329,241 B2 * | 2/2008 | Horvath et al. | 604/208 |
| 7,681,570 B2 * | 3/2010 | Vedrine et al. | 128/200.19 |
| 7,967,010 B2 * | 6/2011 | Vedrine et al. | 128/200.19 |
| 2002/0174864 A1 | 11/2002 | Alchas | |
| 2004/0162528 A1 | 8/2004 | Horvath et al. | |
| 2005/0131354 A1 * | 6/2005 | Tachikawa et al. | 604/187 |
| 2005/0137532 A1 * | 6/2005 | Rolla | 604/218 |
| 2007/0265580 A1 * | 11/2007 | Tachikawa et al. | 604/209 |
| 2008/0097307 A1 * | 4/2008 | Walton et al. | 604/110 |
| 2008/0108952 A1 * | 5/2008 | Horvath et al. | 604/208 |
| 2013/0096493 A1 * | 4/2013 | Kubo et al. | 604/58 |

FOREIGN PATENT DOCUMENTS

| | | |
|---|---|---|
| JP | 2001-137344 A * | 5/2001 |
| JP | 2007-14619 A | 1/2007 |

* cited by examiner

NASAL CAVITY ADMINISTRATION CONTAINER

TECHNICAL FIELD

The present invention relates to a nasal cavity administration container for administering a medical fluid to nasal cavities.

BACKGROUND ART

As disclosed in Japanese Patent Laying-Open No. 2001-137344 (PTD 1), a nasal cavity administration container is used to administer a medical fluid to both the nasal cavities. When the nasal cavity administration container is used, first, with the nasal cavity administration container being inserted in one of the nasal cavities, a predetermined dose of the medical fluid is administered to the one of the nasal cavities. Then, with the nasal cavity administration container being inserted in the other nasal cavity, the remaining medical fluid is administered to the other nasal cavity.

When administering a medical fluid to both the nasal cavities, it is desired that the nasal cavity administration container administer a predetermined dose of the medical fluid (e.g., one half for each) to each nasal cavity easily and appropriately.

CITATION LIST

Patent Document

PTD 1: Japanese Patent Laying-Open No. 2001-137344

SUMMARY OF INVENTION

Technical Problem

The present invention is to provide a nasal cavity administration container that can achieve easier and more appropriate administration when administering a medical fluid to both the nasal cavities.

Solution to Problem

A nasal cavity administration container according to the present invention includes a body section including a medical fluid storage section provided with a spray nozzle on one end side and an opening on the other end side and a plunger to be inserted into the medical fluid storage section from the one end side through the opening, the plunger being provided with a pressing part on the other end side, and a plunger moving amount regulation member including a stopper arranged between the pressing part and the opening and being engaged with the body section, an engagement with the body section being relieved only in a state where the pressing part abuts on the stopper. The plunger is pushed into the medical fluid storage section, thereby moving forward until the pressing part abuts on the stopper. The plunger is further pushed into the medical fluid storage section with the plunger moving amount regulation member detached from the body section.

Preferably, a first fitted part is provided on an outer circumferential surface of the body section, the plunger moving amount regulation member has a second fitted part to be fitted to the first fitted part in a state where the plunger moving amount regulation member is attached to the body section, and a movement of the plunger moving amount regulation member attached to the body section relative to the body section is regulated by a fit between the first fitted part and the second fitted part.

Preferably, the plunger moving amount regulation member has a grasping part to be engaged with the plunger so as to externally grasp the plunger, a constricted part is provided on the other end side of the plunger, and in a state where the pressing part abuts on the stopper, the grasping part is positioned to be opposed to the constricted part, and an engagement of the plunger moving amount regulation member with the plunger is relieved.

Preferably, the plunger has a first abutting part relieving an engagement between the first fitted part and the second fitted part with the pressing part abutting on the stopper.

Preferably, the plunger has a second abutting part located between the stopper and the pressing part in the state where the plunger moving amount regulation member is engaged with the body section, the plunger is inserted into the medical fluid storage section to cause the second abutting part to abut on one of the stopper and the body section, and the plunger is pushed into the medical fluid storage section, thereby relieving an abutment of the plunger on one of the stopper and the body section.

Advantageous Effects of Invention

According to the present invention, a nasal cavity administration container that can achieve easier and more appropriate administration when administering a medical fluid to both the nasal cavities can be obtained.

DESCRIPTION OF EMBODIMENTS

Figure 1:
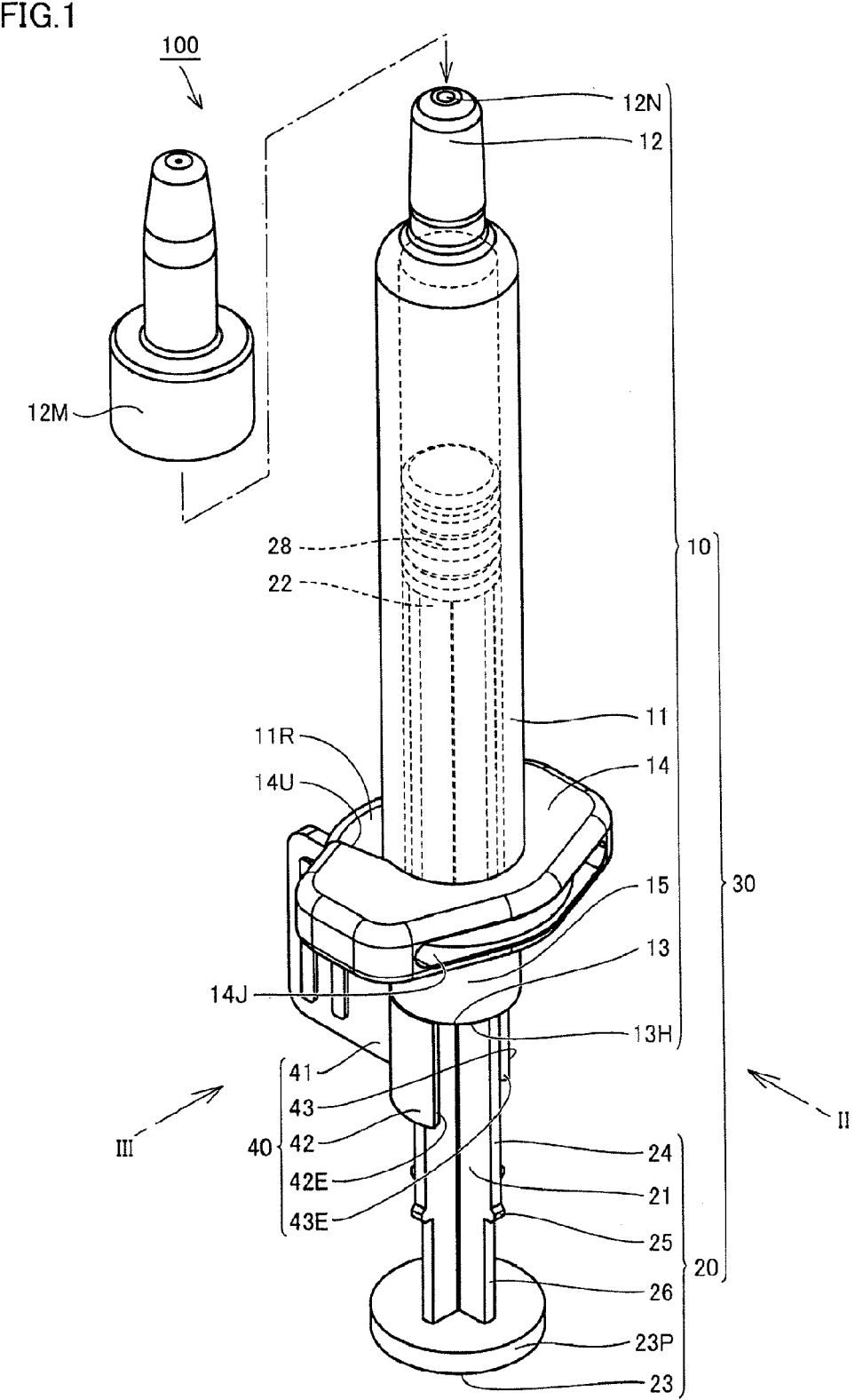
FIG. 1 is a perspective view showing a nasal cavity administration container according to a first embodiment.

Hereinafter, each embodiment based on the present invention will be described with reference to the drawings. When the number, an amount or the like is mentioned in the embodiments described below, the scope of the present invention is not necessarily limited to that number, that amount or the like, unless otherwise specified. In the embodiments described below, the same or corresponding portions have the same reference characters allotted, and overlapping description thereof may not be repeated.

First Embodiment

Structure of Nasal Cavity Administration Container 100

Referring to FIGS. 1 to 6, the structure of a nasal cavity administration container 100 according to the present embodiment will be described.

Figure 2:
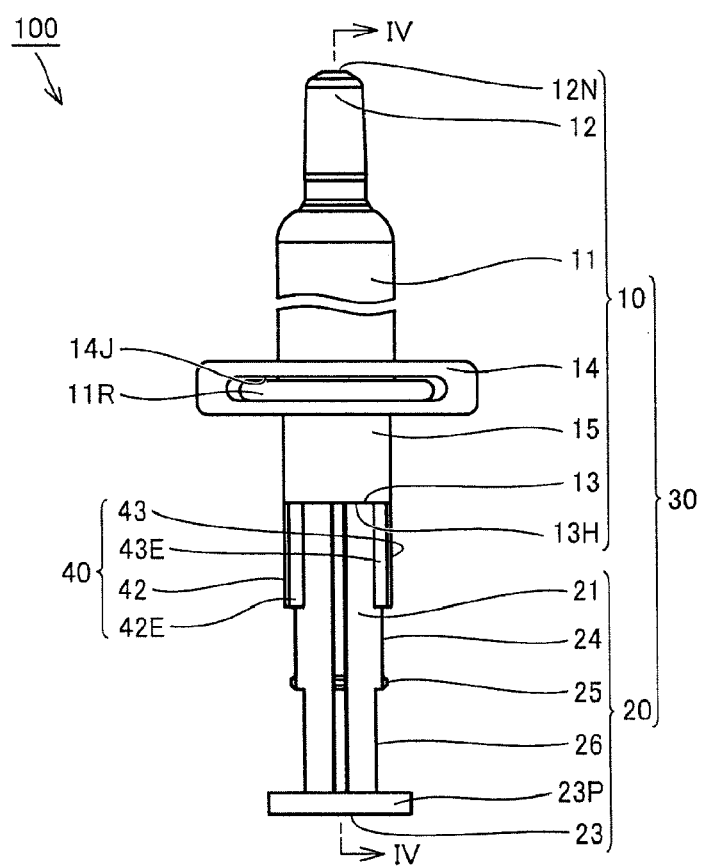
FIG. 2 is a front view showing the nasal cavity administration container according to the first embodiment, which is an arrow view taken along an arrow II in FIG. 1.
Figure 3:
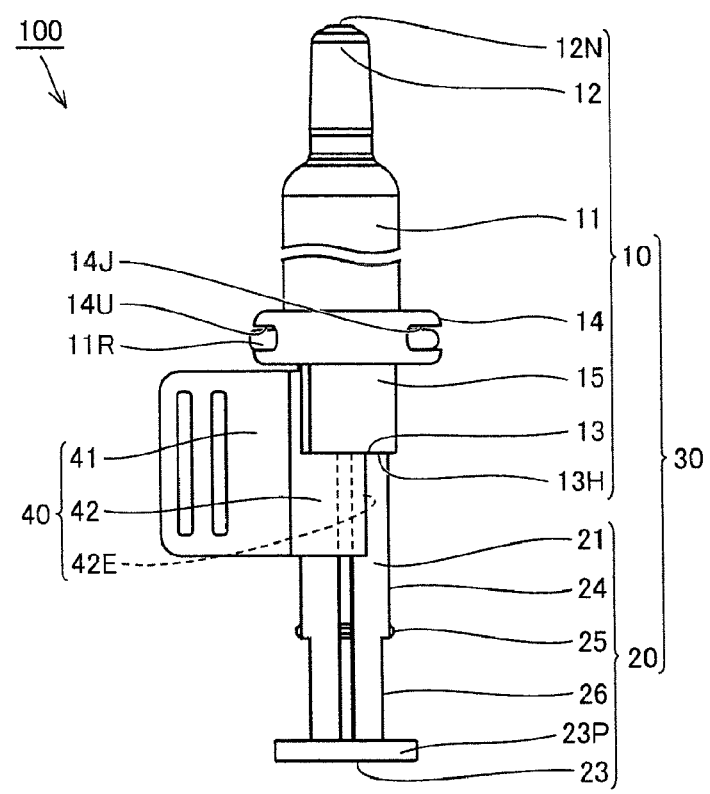
FIG. 3 is a side view showing the nasal cavity administration container according to the first embodiment, which is an arrow view taken along an arrow III in FIG. 1.

FIG. 1 is a perspective view showing nasal cavity administration container 100. FIG. 2 is a front view showing nasal cavity administration container 100, which is an arrow view taken along an arrow II in FIG. 1. FIG. 3 is a side view showing nasal cavity administration container 100, which is an arrow view taken along an arrow III in FIG. 1.

As shown in FIGS. 1 to 3, nasal cavity administration container 100 is provided with a body section 30 and a plunger moving amount regulation member 40. Body section 30 includes a medical fluid storage section 10 and a plunger 20.

Medical Fluid Storage Section 10

Medical fluid storage section 10 is composed of a barrel 11 and a finger clip part 14. Barrel 11 has a substantially cylindrical hollow shape. Plunger 20 and a gasket 28 which will be described later are inserted into barrel 11. One end of barrel 11 constitutes one end 12 of medical fluid storage section 10. A nozzle 12N (syringe nozzle) is formed on the one end 12 side of medical fluid storage section 10. A spray nozzle 12M (see FIG. 1) communicating with the inside of barrel 11 by way of nozzle 12N is attached to the one end 12 side of medical fluid storage section 10. Although spray nozzle 12M illustrated in FIG. 1 is not illustrated in the other drawings, spray nozzle 12M shall be attached to barrel 11 in each of the present and subsequent embodiments. Barrel 11 and spray nozzle 12M may be formed integrally, or may be formed as separate units and then attached to each other as in the present embodiment.

Figure 4:
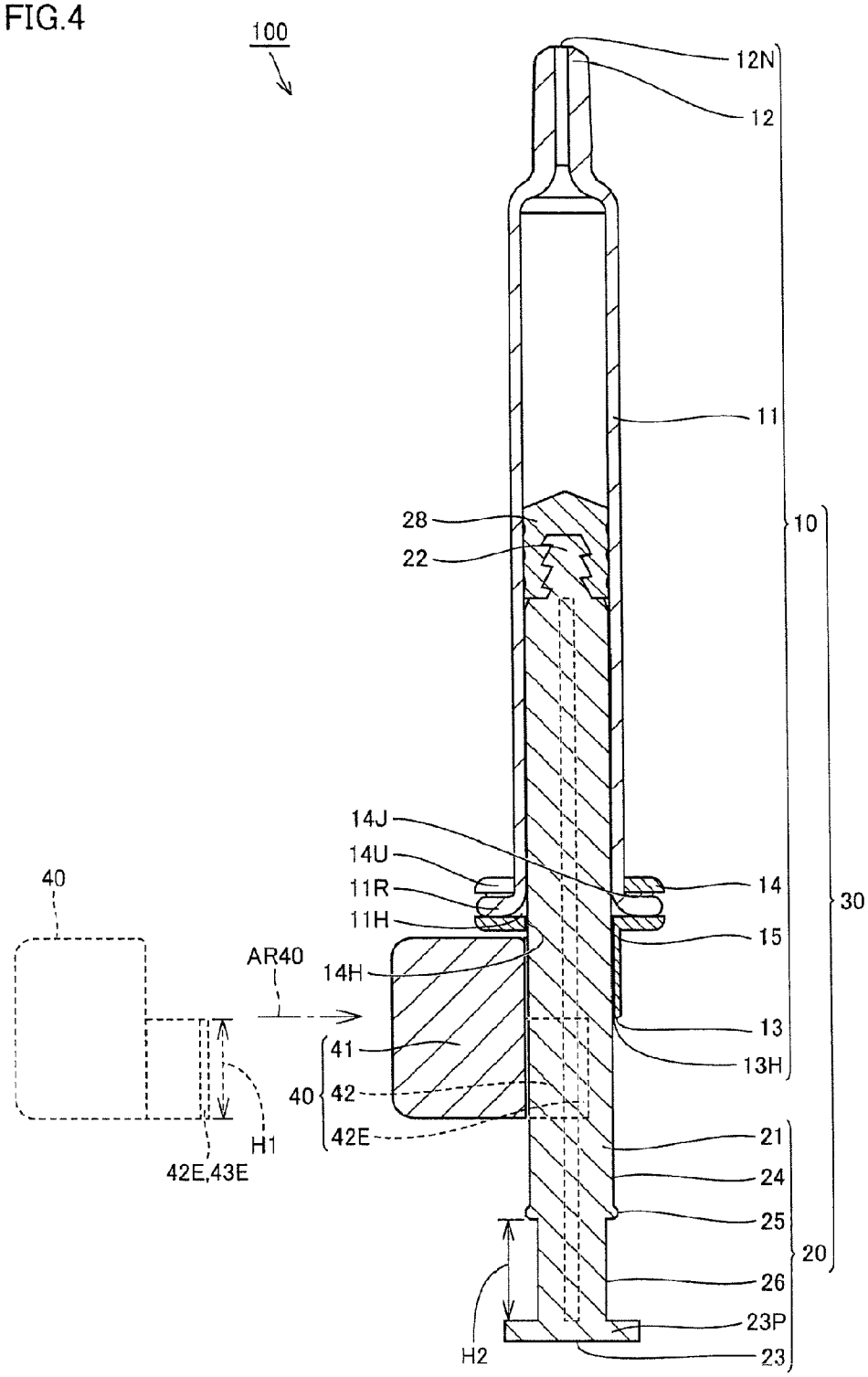
FIG. 4 is an arrow cross sectional view taken along the line IV-IV in FIG. 2.

FIG. 4 is an arrow cross sectional view taken along the line IV-IV in FIG. 2. As shown in FIG. 4 (and FIG. 1), an annular flange part 11R bulging outwardly in a cylinder radial direction is provided on the other end side of barrel 11. On the inner side relative to flange part 11R, an opening 11H (see FIG. 4) communicating with the inside of barrel 11 is formed.

Finger clip part 14 is provided with a notch 14U corresponding to the outer shape of flange part 11R (see FIG. 1 as well). Notch 14U communicates with an opening 14J extending through toward the outer edge of finger clip part 14. Finger clip part 14 is attached to flange part 11R by frictional engagement while grasping flange part 11R.

Finger clip part 14 is also provided with an opening 14H (see FIG. 4) through which plunger 20 and gasket 28 pass. A suspended part 15 is provided to hang down continuously with opening 14H. Suspended part 15 has a substantially halved cylindrical shape. The leading end of suspended part 15 in the hanging down direction constitutes the other end 13 of medical fluid storage section 10. An opening 13H through which plunger 20 and gasket 28 pass is formed on the other end 13 side of medical fluid storage section 10.

Plunger 20

Figure 5:
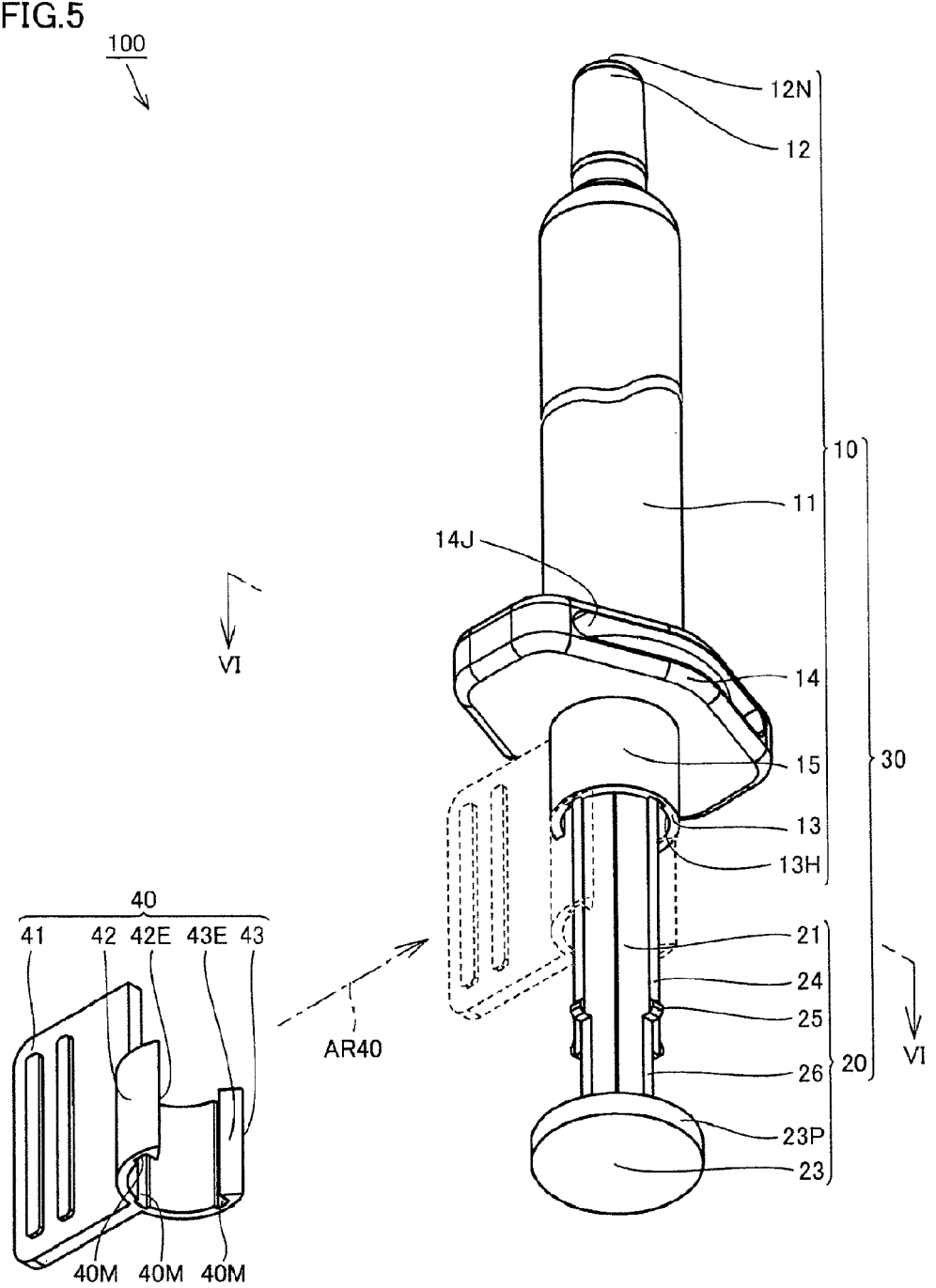
FIG. 5 is a perspective view showing a state where the nasal cavity administration container according to the first embodiment has been disassembled partly (a plunger moving amount regulation member has been detached from a body section).

FIG. 5 is a perspective view showing a state where nasal cavity administration container 100 has been disassembled partly (plunger moving amount regulation member 40 has been detached from body section 30). As shown in FIG. 5 (and FIG. 4), plunger 20 has a substantially rod-like shape. Plunger 20 has four ribs 21 having a thin plate shape.

Four ribs 21 extend in the longitudinal direction of plunger 20 from one end 22 (see FIG. 4) toward the other end 23 (see FIG. 4) of plunger 20. As shown in FIG. 5, four ribs 21 are arranged at 90° intervals, and stand up toward the outside perpendicularly to the longitudinal direction of plunger 20.

Referring again to FIG. 4, gasket 28 made of rubber is provided on one end 22 of plunger 20. A disc-like pressing part 23P is provided on the other end 23 of plunger 20. As described above, plunger 20 is inserted into medical fluid storage section 10 (barrel 11) together with gasket 28 from the one end 22 side through opening 13H of medical fluid storage section 10 (barrel 11).

A constricted part 26 is provided on the other end 23 side of plunger 20 according to the present embodiment. The height of constricted part 26 (a dimension of plunger 20 in the direction perpendicular to the longitudinal direction of plunger 20 (in the horizontal direction on the sheet of FIG. 4)) is established relatively low as compared with a leading end 24 in the direction in which each rib 21 stands up. In other words, each rib 21 is constricted at constricted part 26.

Each of four ribs 21 is provided with an abutting part 25 (second abutting part) between leading end 24 and constricted part 26. It is noted that abutting part 25 may be provided according to necessity. When abutting part 25 is provided between leading end 24 and constricted part 26, abutting part 25 is provided to project from leading end 24 of rib 21 in the direction perpendicular to the longitudinal direction of plunger 20. The leading end of abutting part 25 in the projecting direction is positioned at a slightly outer side (in the horizontal direction on the sheet of FIG. 4) relative to the inner diameter of suspended part 15 of finger clip part 14. Further details of abutting part 25 and constricted part 26 will be described later.

Plunger Moving Amount Regulation Member 40

Referring again to FIG. 5, plunger moving amount regulation member 40 includes a grip 41 and stoppers 42 and 43. Stoppers 42 and 43 are formed continuously with an end of grip 41 having a flat plate-like shape. Stoppers 42 and 43 are formed symmetrically on the opposite sides of grip 41, and present a substantially halved cylindrical shape as a whole.

Figure 6:
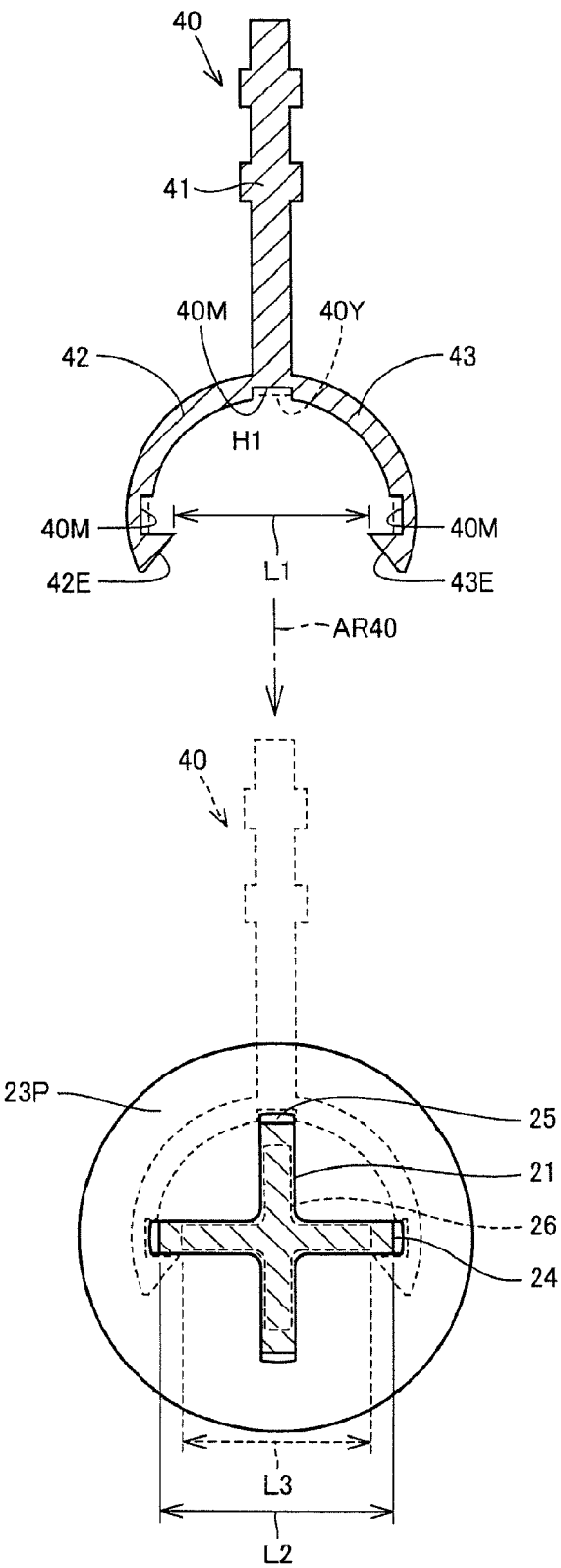
FIG. 6 is an arrow cross sectional view taken along the line VI-VI in FIG. 5.

FIG. 6 is an arrow cross sectional view taken along the line VI-VI in FIG. 5. As shown in FIG. 6, a grasping part 42E is provided at the leading end of stopper 42. Grasping part 42E is formed to be folded back from the leading end of stopper 42 toward the inner side. A grasping part 43E is provided at the leading end of stopper 43. Grasping part 43E is also formed to be folded back from the leading end of stopper 43 toward the inner side.

A distance L1 between grasping parts 42E and 43E is provided to be slightly smaller than a distance L2 between leading ends 24 in the standing direction of ribs 21 (distance L1<distance L2) Plunger moving amount regulation member 40 can be engaged with plunger 20 so as to grip ribs 21 (leading ends 24 of ribs 21) of plunger 20 from the outside by means of grasping parts 42E and 43E.

On the other hand, distance L1 between grasping parts 42E and 43E is provided to be slightly wider than a distance L3 between the leading ends of constricted parts 26 (distance L1>distance L3). Furthermore, as shown in FIG. 4, a dimension H1 of grasping parts 42E and 43E in the longitudinal direction is provided to be slightly smaller than a dimension H2 of constricted part 26 of plunger 20 in the same direction (dimension H1<dimension H2). In the state where grasping parts 42E, 43E and constricted parts 26 are arranged to be opposed to each other, plunger moving amount regulation member 40 is not engaged with plunger 20.

As shown in FIGS. 5 and 6, long slots 40M may be provided in the inner circumferential side of stoppers 42 and 43. Long slots 40M are formed to correspond to the shape of ribs 21 of plunger 20. When leading ends 24 of ribs 21 and long slots 40M are fitted to each other in the state where plunger moving amount regulation member 40 is attached to plunger 20 (in the state where grasping parts 42E and 43E of plunger moving amount regulation member 40 and ribs 21 of plunger 20 are engaged with each other), a rotational movement of plunger moving amount regulation member 40 relative to plunger 20 can be restrained or prevented. A rib 40Y (see FIG. 6) may be provided in long slots 40M (the operation of rib 40Y will be described later).

Assembly of Nasal Cavity Administration Container 100

Referring again to FIG. 4, when nasal cavity administration container 100 is assembled, first, gasket 28 is inserted into barrel 11 through opening 11H of barrel 11. Before inserting gasket 28 into barrel 11, a rubber cap or the like may be attached to one end 12 of barrel 11, and in this state, barrel 11 may be filled up with a medical fluid.

After barrel 11 is filled up with the medical fluid according to necessity, plunger 20 is attached to gasket 28. Finger clip part 14 is attached to flange part 11R of barrel 11. As described above, finger clip part 14 is attached to flange part 11R by frictional engagement while holding flange part 11R.

Then, plunger moving amount regulation member 40 is attached to plunger 20 (see arrow AR40). When attaching plunger moving amount regulation member 40 to plunger 20, plunger moving amount regulation member 40 is brought closer to finger clip part 14. Since grasping parts 42E and 43E are engaged with ribs 21, stoppers 42 and 43 of plunger moving amount regulation member 40 are slightly elastically deformed to the outside.

When grasping parts 42E and 43E have passed over ribs 21, stoppers 42 and 43 are engaged with plunger 20. Moreover, as described above, spray nozzle 12M (see FIG. 1) is attached to one end 12 of barrel 11. As described above, nasal cavity administration container 100 is assembled.

It is noted that plunger moving amount regulation member 40 may be attached to body section 30 (plunger 20) in the following manner. First, plunger 20 is inserted into medical fluid storage section 10 to cause abutting part 25 of plunger 20 to abut on the other end 13 of suspended part 15. In the state where the relative positional relationship between medical fluid storage section 10 and plunger 20 is fixed, constricted parts 26 of plunger 20 and stoppers 42, 43 of plunger moving amount regulation member 40 are arranged to be opposed to each other. Plunger moving amount regulation member 40 and plunger 20 are arranged adjacent to each other such that stoppers 42 and 43 of plunger moving amount regulation member 40 surround the outer circumferences of constricted parts 26.

Next, in the state where the relative positional relationship between plunger moving amount regulation member 40 and medical fluid storage section 10 is fixed, plunger 20 is moved away from medical fluid storage section 10. When abutting part 25 of plunger 20 passes by the inner side of stoppers 42 and 43 of plunger moving amount regulation member 40, stoppers 42 and 43 are slightly elastically deformed to the outside. When abutting part 25 has completely passed by the inner side of stoppers 42 and 43, a state similar to that shown in FIG. 4 is obtained. Nasal cavity administration container 100 may be assembled in this manner.

Referring again to FIG. 1, in the state where nasal cavity administration container 100 has been assembled, stoppers 42 and 43 of plunger moving amount regulation member 40 are located between pressing part 23P of plunger 20 and opening 13H of medical fluid storage section 10 (finger clip part 14). Plunger moving amount regulation member 40 is engaged with body section 30 (specifically, ribs 21 of plunger 20) by means of grasping parts 42E and 43E. Abutting part 25 of plunger 20 is located between stoppers 42, 43 of plunger moving amount regulation member 40 and pressing part 23P of plunger 20.

As described above, in nasal cavity administration container 100, the relationships in which distance L1<distance L2 in FIG. 6, distance L1>distance L3 in FIG. 6, and dimension H1<dimension H2 in FIG. 4 hold. As will be described later in detail referring to FIG. 9, this structure allows the state where plunger moving amount regulation member 40 is engaged with body section 30 to be relieved only in the state where pressing part 23P of plunger 20 abuts on stoppers 42, 43 of plunger moving amount regulation member 40 (the state shown in FIG. 9).

Operation of Nasal Cavity Administration Container 100

Referring to FIGS. 7 to 12, the operation of nasal cavity administration container 100 will be described. Nasal cavity administration container 100 transitions sequentially among the respective states of a first administration preparatory state S11 (see FIG. 7), a first administration start state S12 (see FIG. 8), a first administration completion state S13 (see FIG. 9), a second administration preparatory state S14 (see FIG. 10), a second administration start state S15 (see FIG. 11), and a second administration completion state S16 (see FIG. 12).

As will be described later in detail, a first administration of a medical fluid 60 is carried out through first administration preparatory state S11, first administration start state S12 and first administration completion state S13. A second administration of medical fluid 60 is carried out through second administration preparatory state S14, second administration start state S15 and second administration completion state S16.

First Administration Preparatory State S11

Figure 7:
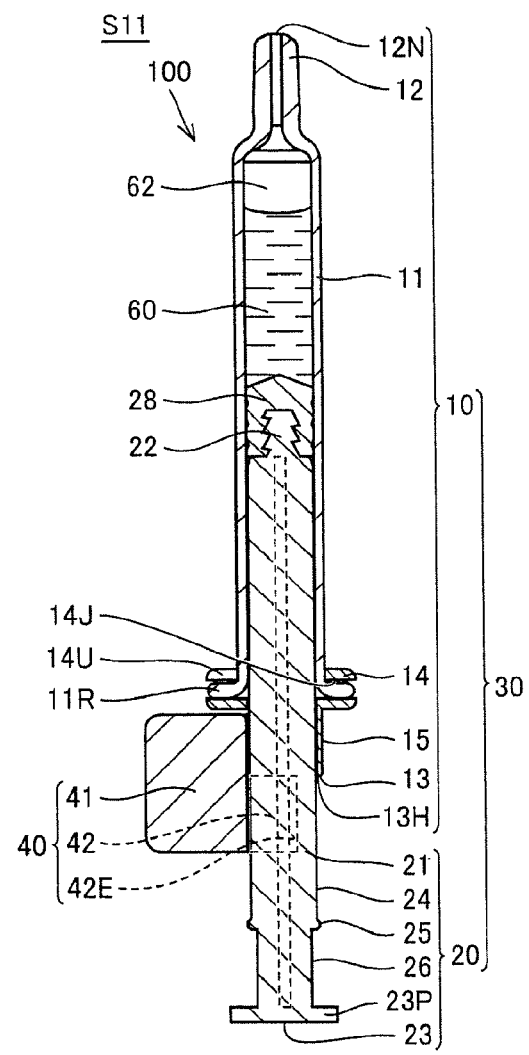
FIG. 7 is a cross sectional view showing a first administration preparatory state of the nasal cavity administration container according to the first embodiment.

Referring to FIG. 7, medical fluid 60 is injected (or sucked) into nasal cavity administration container 100 as assembled from the nozzle 12N side (the state shown in FIG. 7). When injection of medical fluid 60 is completed, nasal cavity administration container 100 transitions to first administration preparatory state S11. In this occasion, air 62 may enter medical fluid storage section 10 (barrel 11) on the one end 12 side.

First Administration Start State S12

Figure 8:
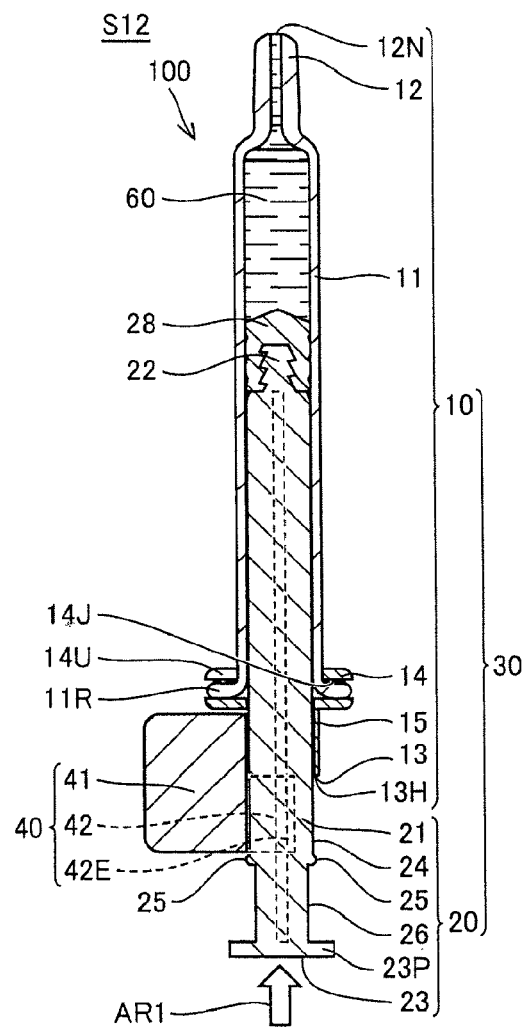
FIG. 8 is a cross sectional view showing a first administration start state of the nasal cavity administration container according to the first embodiment.

Referring to FIG. 8, an operation called priming is carried out for the purpose of setting the dose of medical fluid 60 to be administered to a nasal cavity at a predetermined value and exhausting air having entered medical fluid storage section 10 (barrel 11) (according to necessity).

Specifically, plunger 20 is inserted into medical fluid storage section 10 (barrel 11) (see arrow AR1). Plunger 20 and gasket 28 enter barrel 11 while in sliding contact with the inside of barrel 11 until abutting part 25 of plunger 20 abuts on stoppers 42 and 43 of plunger moving amount regulation member 40. A rib (above-described rib 40Y in FIG. 6) to abut on abutting part 25 when plunger 20 is inserted into barrel 11 may be provided on the inner side of stoppers 42 and 43. By providing rib 40Y, abutting part 25 of plunger 20 abuts on this rib 40Y. Plunger 20 enters barrel 11 until this abutting is accomplished.

When abutting part 25 of plunger 20 abuts on stoppers 42, 43 of plunger moving amount regulation member 40 (or rib 40Y provided on the inner side of stoppers 42 and 43), the movement of plunger moving amount regulation member 40 relative to body section 30 is stopped (the state shown in FIG. 8). According to the present embodiment, stoppers 42 and 43 correspond to "one of stoppers 42, 43 and body section 30."

When the movement of plunger moving amount regulation member 40 relative to body section 30 is stopped, nasal cavity administration container 100 transitions to first administration start state S12. The air in medical fluid storage section 10 (barrel 11) is forced out of medical fluid storage section 10, and the dose of medical fluid 60 to be administered to a nasal cavity is set at the predetermined value (priming is carried out).

First Administration Completion State S13

Figure 9:
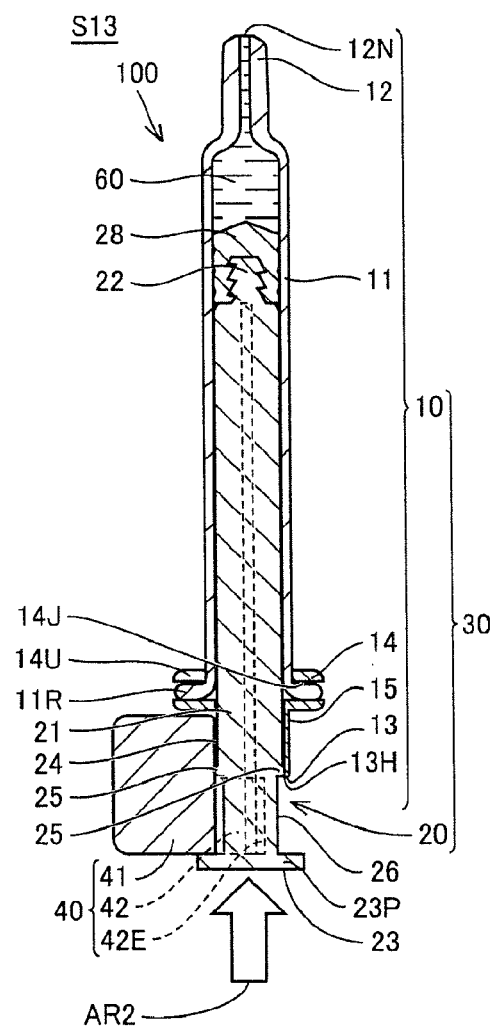
FIG. 9 is a cross sectional view showing a first administration completion state of the nasal cavity administration container according to the first embodiment.

Referring to FIG. 9, after the dose of medical fluid 60 to be administered to a nasal cavity is set at the predetermined value, spray nozzle 12M (see FIG. 1) attached to the nozzle 12N side is located in one of the nasal cavities. In this state, plunger 20 is strongly pushed into medical fluid storage section 10 (barrel 11) by means of pressing part 23P (see arrow AR2).

By vigorously pushing plunger 20, the state where abutting part 25 of plunger 20 abuts on stoppers 42, 43 of plunger moving amount regulation member 40 (or rib 40Y provided on the inner side of stoppers 42, 43) is relieved. Plunger 20 moves forward inside medical fluid storage section 10 while abutting part 25 enters toward the inner side of stoppers 42, 43. Gasket 28 is pushed by plunger 20, thereby entering medical fluid storage section 10. It is noted that, since rib 40Y is provided on the inner side of stoppers 42, 43, abutting part 25 and rib 40Y are engaged with each other until compressive force stronger than prescribed is applied, which enables stable spray into a nasal cavity under high pressure from the start of spraying.

Medical fluid 60 in medical fluid storage section 10 is sprayed through spray nozzle 12M (see FIG. 1) by the movement of gasket 28. A mist of medical fluid 60 is administered to one of the nasal cavities through spray nozzle 12M. Plunger 20 moves forward until pressing part 23P abuts on the lower ends of stoppers 42, 43 of plunger moving amount regulation member 40.

When pressing part 23P abuts on the lower ends of stoppers 42, 43 of plunger moving amount regulation member 40, the movement of plunger 20 relative to medical fluid storage section 10 is stopped (the state shown in FIG. 9). When the movement of plunger 20 is stopped, the first administration is completed, and nasal cavity administration container 100 transitions to first administration completion state S13. The amount of stroke of plunger 20 relative to medical fluid storage section 10 defines the first dosage of medical fluid 60.

Second Administration Preparatory State S14

Figure 10:
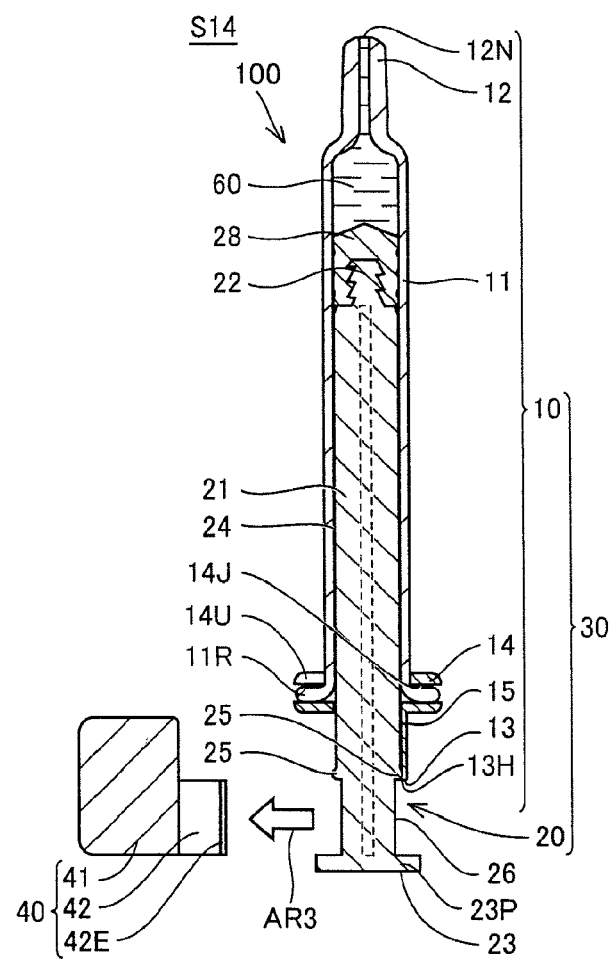
FIG. 10 is a cross sectional view showing a second administration preparatory state of the nasal cavity administration container according to the first embodiment.

Referring to FIG. 10, in the state where the first administration of medical fluid 60 has been completed (the state shown in FIG. 9), grasping parts 42E and 43E of plunger moving amount regulation member 40 are positioned to be opposed to constricted parts 26 of plunger 20. The state where plunger moving amount regulation member 40 is engaged with plunger 20 (ribs 21) is relieved by the arrangement relationship between grasping parts 42E, 43E and constricted parts 26.

In order to perform the second administration of medical fluid 60, plunger moving amount regulation member 40 is detached from body section 30 (the state shown in FIG. 10) as indicated by arrow AR3. When plunger moving amount regulation member 40 is detached from body section 30, nasal cavity administration container 100 transitions to second administration preparatory state S14.

Second Administration Start State S15

Figure 11:
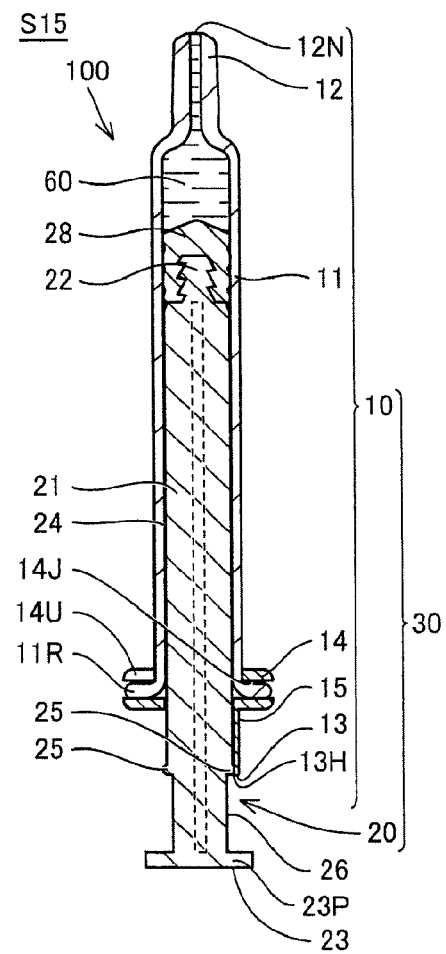
FIG. 11 is a cross sectional view showing a second administration start state of the nasal cavity administration container according to the first embodiment.

Referring to FIG. 11, after plunger moving amount regulation member 40 is detached from body section 30 (after second administration preparatory state S14), spray nozzle 12M (see FIG. 1) attached on the nozzle 12N side of nasal cavity administration container 100 is located in the other nasal cavity. Nasal cavity administration container 100 thereby transitions to second administration start state S15.

Second Administration Completion State S16

Figure 12:
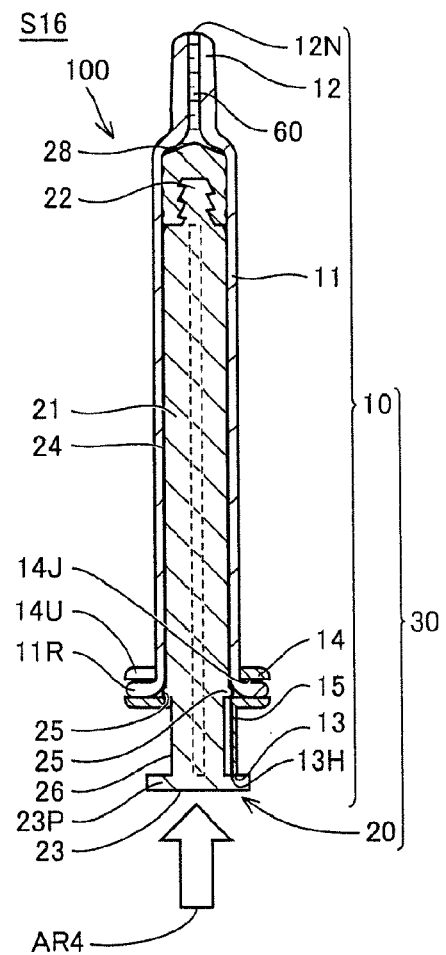
FIG. 12 is a cross sectional view showing a second administration completion state of the nasal cavity administration container according to the first embodiment.

Referring to FIG. 12, after spray nozzle 12M (see FIG. 1) of nasal cavity administration container 100 is located in the other nasal cavity, plunger 20 is further pushed into medical fluid storage section 10 (barrel 11) by means of pressing part 23P (see arrow AR4). Plunger 20 moves forward inside medical fluid storage section 10. Gasket 28 is pushed by plunger 20, thereby further entering medical fluid storage section 10.

A rib having a function similar to above-described rib 14Y (see FIG. 6) may be provided on the inner side of suspended part 15 of finger clip part 14. When plunger 20 is further pushed into barrel 11, abutting part 25 is engaged with this rib. Since abutting part 25 and this rib are engaged until compressive force stronger than prescribed is applied, stable spray into the nasal cavities can be accomplished under high pressure from the start of spraying.

Medical fluid 60 in medical fluid storage section 10 is sprayed through spray nozzle 12M (see FIG. 1) by the movement of gasket 28. A mist of medical fluid 60 is administered through spray nozzle 12M to the other nasal cavity. Plunger 20 moves forward until gasket 28 abuts on the upper end in barrel 11. Plunger 20 may be formed to move forward until pressing part 23P abuts on the lower end (other end 13) of suspended part 15 of finger clip part 14.

When plunger 20 is moved forward until gasket 28 abuts on the upper end in barrel 11, the movement of plunger 20 relative to medical fluid storage section 10 is stopped (the state shown in FIG. 12). When the movement of plunger 20 is stopped, the second administration is completed, and nasal cavity administration container 100 transitions to second administration completion state S16. The amount of stroke of plunger 20 relative to medical fluid storage section 10 defines the second dosage of medical fluid 60. Nasal cavity administration container 100 operates as described above, and the administration of medical fluid 60 by nasal cavity administration container 100 is carried out as described above.

Function and Effect

In nasal cavity administration container 100, as described above, abutting part 25 is provided for plunger 20, and plunger moving amount regulation member 40 is attached to plunger 20 of body section 30. When abutting part 25 of plunger 20 abuts on stoppers 42, 43 of plunger moving amount regulation member 40, nasal cavity administration container 100 can easily transition from first administration preparatory state S11 (see FIG. 7) to first administration start state S12 (see FIG. 8). It is noted that abutting part 25 may be provided according to necessity as described above.

In nasal cavity administration container 100, as described above, plunger moving amount regulation member 40 is engaged with body section 30 through first administration preparatory state S11 (see FIG. 7), first administration start state S12 (see FIG. 8) and first administration completion state S13 (see FIG. 9). The state where plunger moving amount regulation member 40 is engaged with body section 30 can be relieved only in the state where pressing part 23P of plunger 20 abuts on stoppers 42, 43 of plunger moving amount regulation member 40.

Since plunger moving amount regulation member 40 is not detached from body section 30 until the first administration of medical fluid 60 is completed, nasal cavity administration container 100 can reliably administer an appropriate dosage. Concurrently with the completion of the first administration of medical fluid 60, plunger moving amount regulation member 40 can be easily detached from body section 30 by means of constricted parts 26 of plunger 20. Nasal cavity administration container 100 is highly convenient in preparation of the second administration after the first administration is completed.

Another Structure of First Embodiment

When the second administration of medical fluid 60 is started (in second administration start state S15 (see FIG. 11)), abutting part 25 of plunger 20 may be formed to come into frictional engagement with the inner circumferential surface of suspended part 15. This structure is obtained by slightly increasing the projecting dimension of abutting part 25 with respect to the inner diameter of suspended part 15.

With this structure, at the start of the second administration, relatively large compressive force is applied to pressing part 23P so as to relieve the frictional engagement of abutting part 25 with the inner circumferential surface of suspended part 15. After the frictional engagement is relieved by the relatively large compressive force, plunger 20 can be vigorously pushed into medical fluid storage section 10 by that force. Medical fluid 60 can also be appropriately administered in a favorable mist form in the second administration.

It is noted that, when the first administration of medical fluid 60 is started, abutting part 25 may similarly be formed so as to come into frictional engagement with the inner circumferential surface of stoppers 42 and 43. With this structure, at the start of the first administration, relatively large compressive force is applied to pressing part 23P so as to relieve the frictional engagement of abutting part 25 with the inner circumferential surface of stoppers 42 and 43. After the frictional engagement is relieved by the relatively large compressive force, plunger 20 can be vigorously pushed into medical fluid storage section 10 by that force. Medical fluid 60 can also be appropriately administered in a favorable mist form in the first administration.

Second Embodiment

Figure 13:
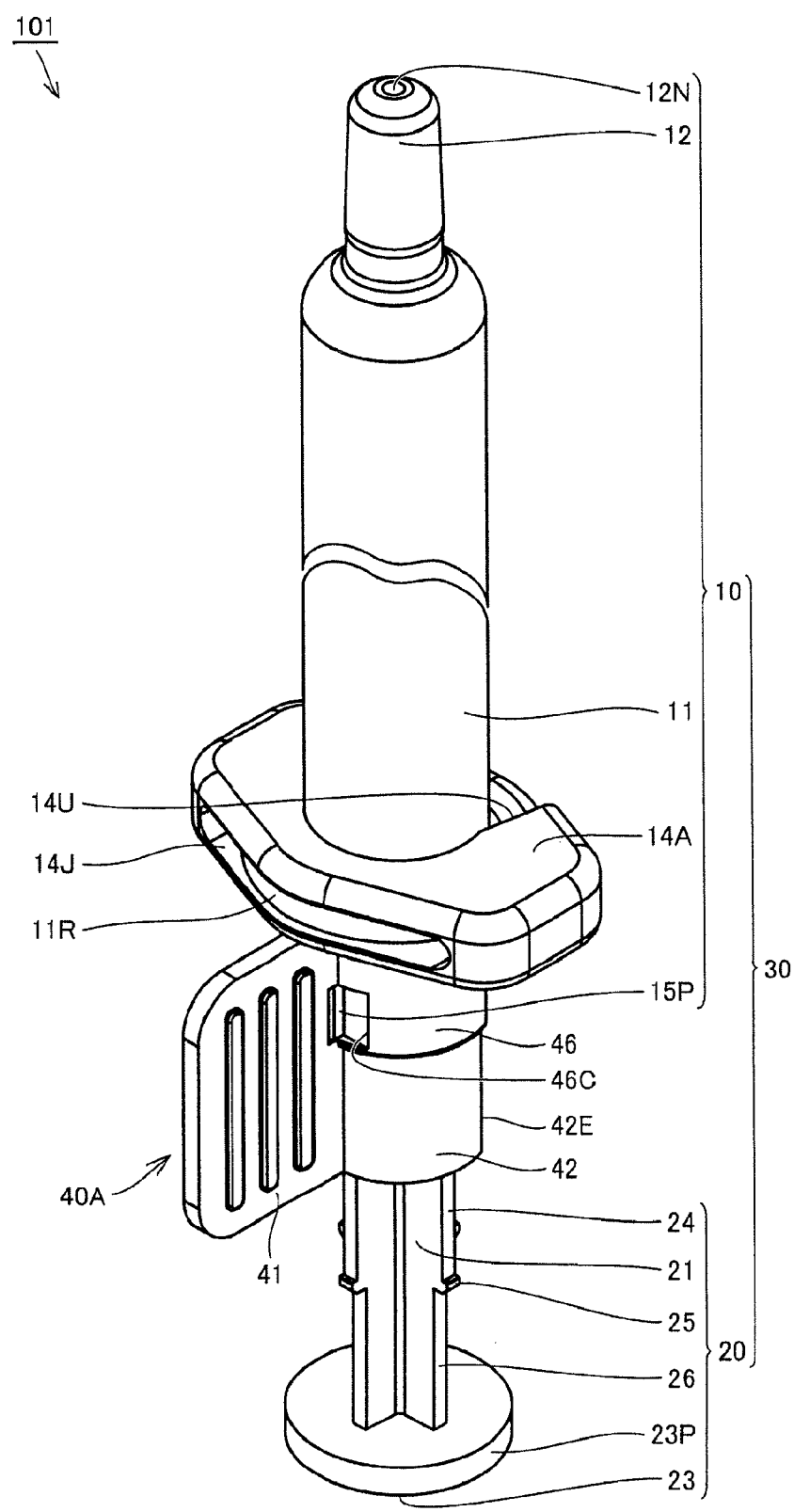
FIG. 13 is a perspective view showing a nasal cavity administration container according to a second embodiment.
Figure 14:
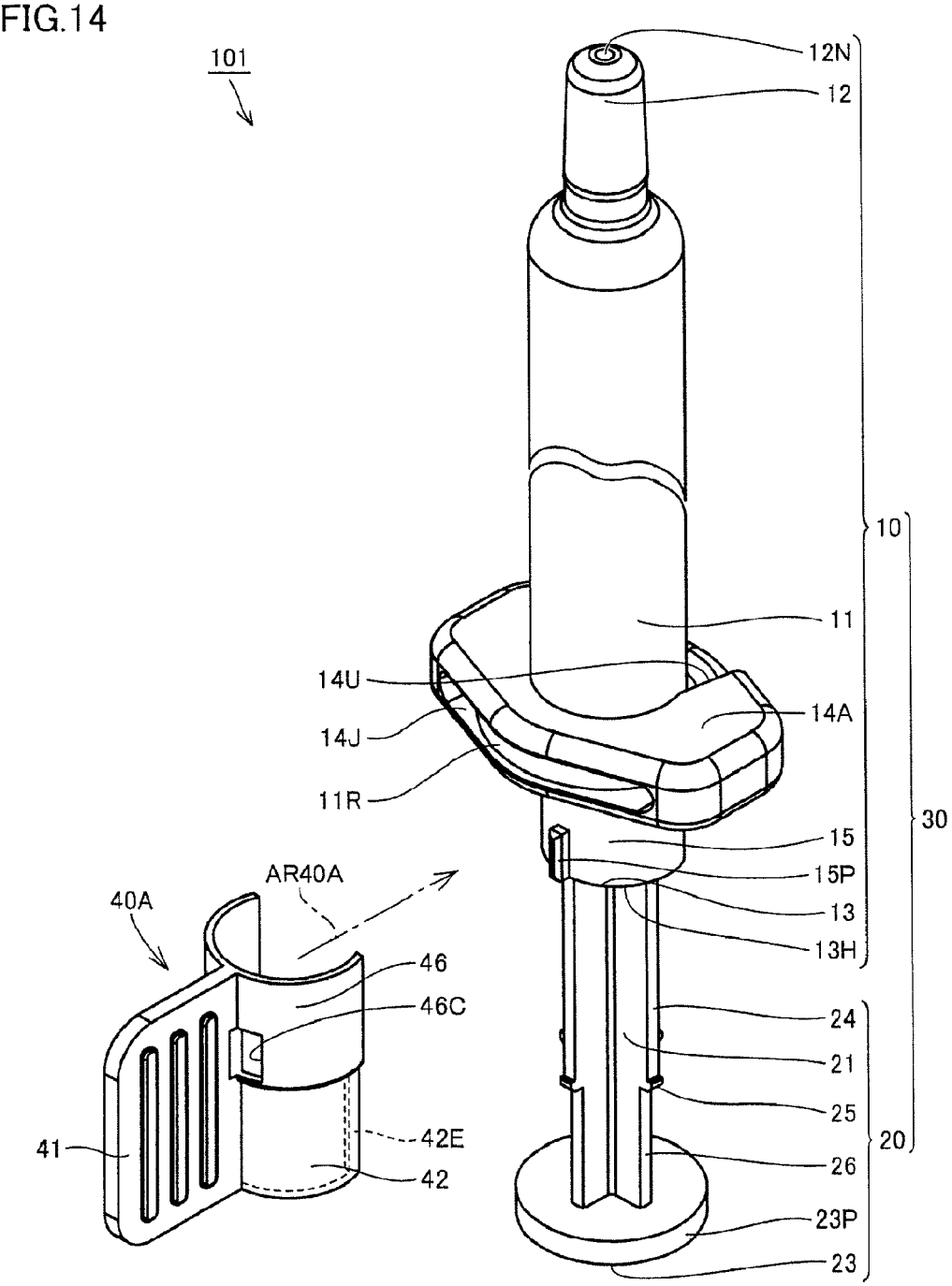
FIG. 14 is a perspective view showing a state where the nasal cavity administration container according to the second embodiment has been disassembled partly (a plunger moving amount regulation member has been detached from the body section).
Figure 15:
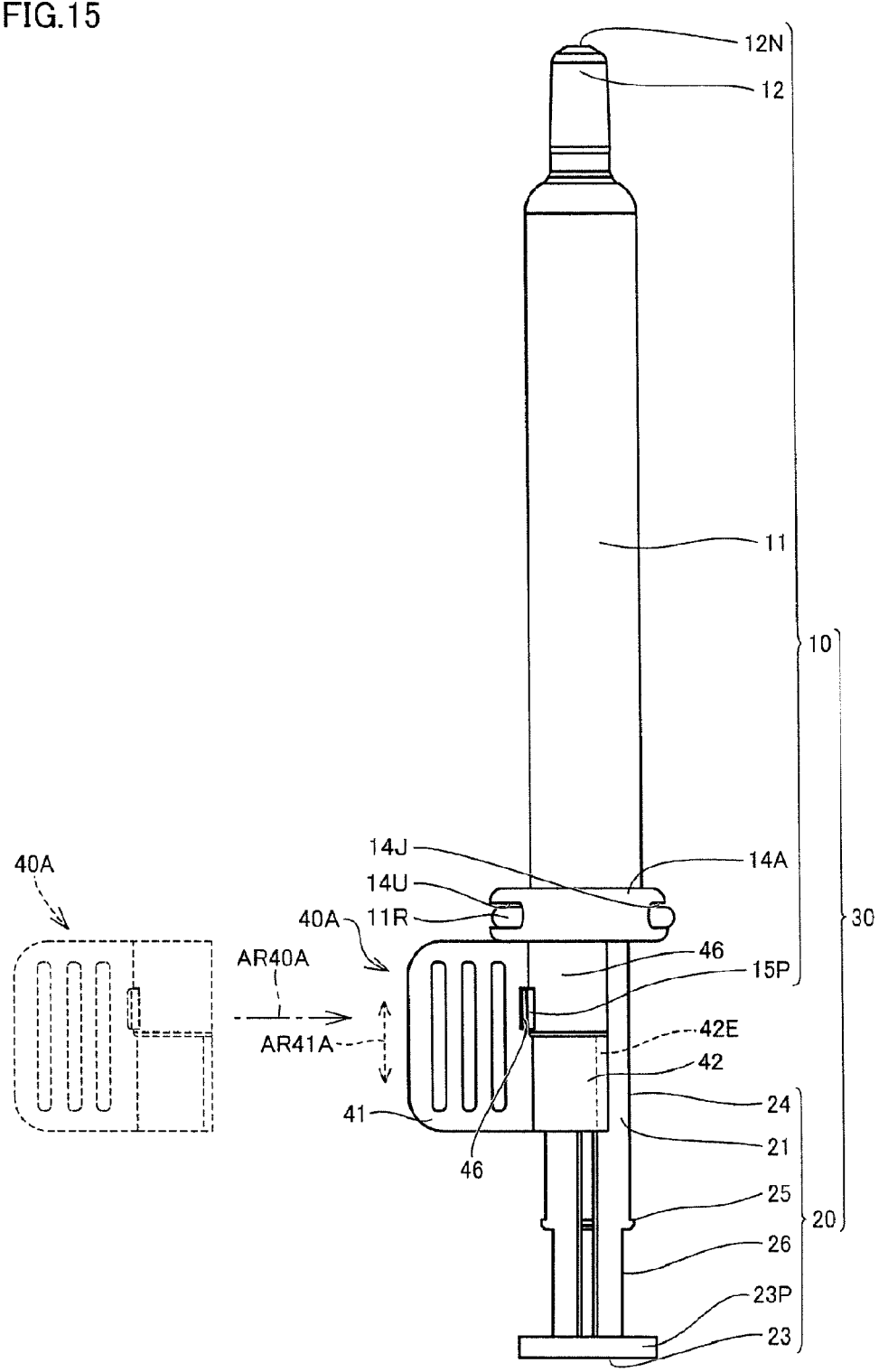
FIG. 15 is a side view showing the nasal cavity administration container according to the second embodiment.

Referring to FIGS. 13 to 15, a nasal cavity administration container 101 according to the present embodiment will be described. Nasal cavity administration container 101 differs from nasal cavity administration container 100 (see FIG. 1) according to the above-described first embodiment in the following points.

FIG. 13 is a perspective view showing nasal cavity administration container 101. As shown in FIG. 13, nasal cavity administration container 101 is provided with body section 30 and a plunger moving amount regulation member 40A. Body section 30 includes medical fluid storage section 10 and plunger 20.

FIG. 14 is a perspective view showing a state where nasal cavity administration container 101 has been disassembled partly (plunger moving amount regulation member 40A has been detached from body section 30). As shown in FIG. 14, medical fluid storage section 10 according to the present embodiment includes a finger clip part 14A. A projection 15P (first fitted part) is provided on the outer circumference of suspended part 15 of finger clip part 14A.

Plunger moving amount regulation member 40A according to the present embodiment is provided with a guard part 46 is provided so as to be adjacent to stoppers 42 and 43 (not shown). Guard part 46 has a halved cylindrical shape. Guard part 46 is provided with an opening 46C (second fitted part) corresponding to the shape of projection 15P provided on suspended part 15.

FIG. 15 is a side view showing nasal cavity administration container 101. As shown in FIG. 15, plunger moving amount regulation member 40A is attached to body section 30 (see arrow AR40A). In this state, projection 15P and opening 46C are fitted to each other. This fit regulates the movement of plunger moving amount regulation member 40A relative to body section 30 in the direction of an arrow AR41A.

It is noted that plunger moving amount regulation member 40A may be attached to body section 30 with abutting part 25 of plunger 20 abutting on the other end 13 of suspended part 15, similarly to the above-described first embodiment. In this case, projection 15P and opening 46C are fitted to each other by attaching plunger moving amount regulation member 40A to body section 30. After projection 15P and opening 46C are fitted to each other, plunger 20 is moved away from medical fluid storage section 10. By such assembly, the state shown in FIG. 13 can also be obtained.

Plunger moving amount regulation member 40A and finger clip part 14A may be previously assembled to each other before finger clip part 14A is attached to flange part 11R. With plunger moving amount regulation member 40A and finger clip part 14A integrated together, plunger moving amount regulation member 40A and finger clip part 14A can be easily attached to barrel 11 (flange part 11R).

In nasal cavity administration container 101, the first administration and the second administration are each carried out similarly to the above-described first embodiment. At the time of the first administration, the movement of plunger moving amount regulation member 40A relative to body section 30 in the direction of arrow AR41A (see FIG. 15) is regulated. Since plunger moving amount regulation member 40A is fixed relative to body section 30, nasal cavity administration container 101 presents excellent operational stability when pushing plunger 20 into medical fluid storage section 10.

Third Embodiment

Figure 16:
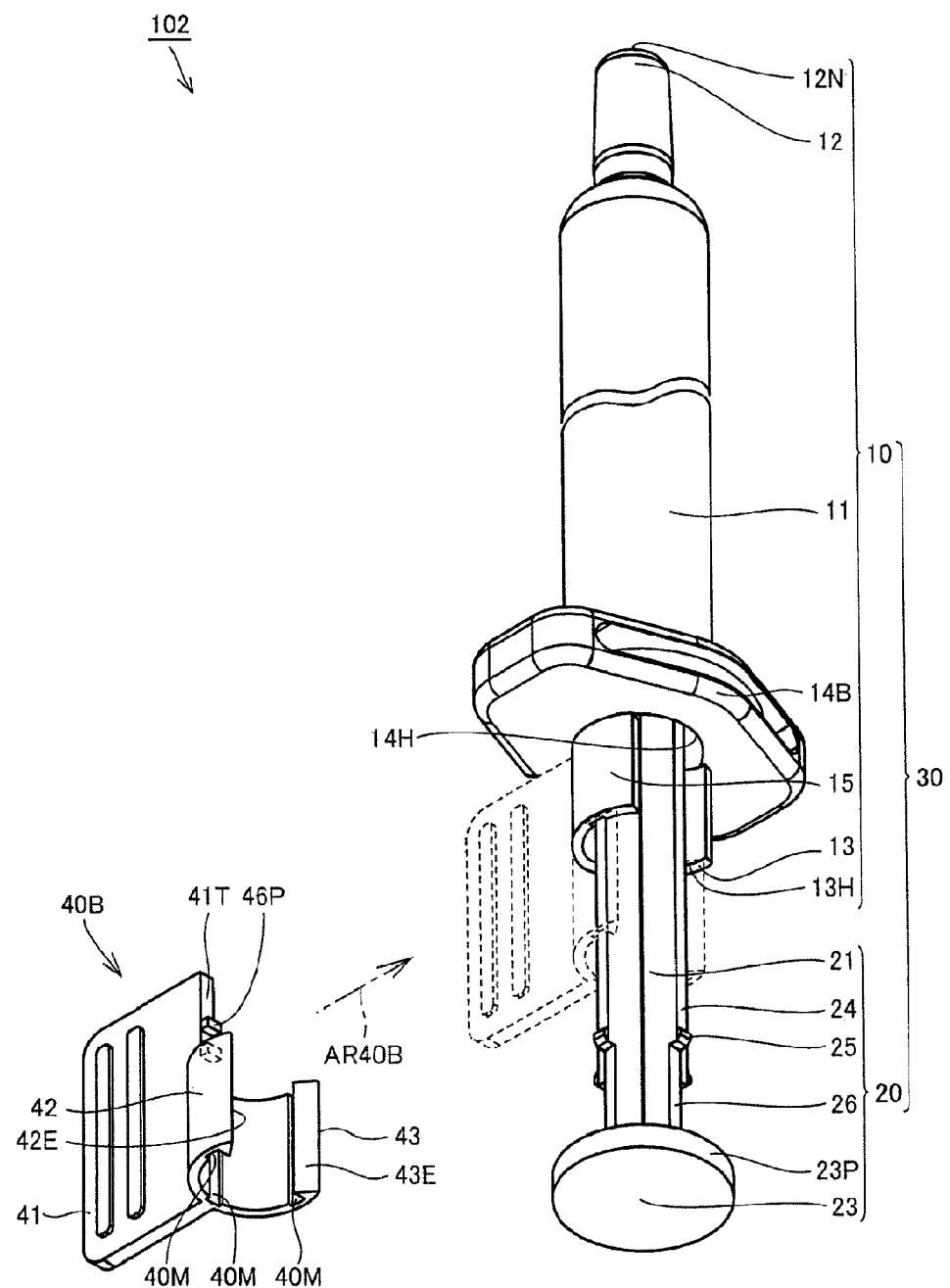
FIG. 16 is a first perspective view showing a state where a nasal cavity administration container according to a third embodiment has been disassembled partly (a plunger moving amount regulation member has been detached from the body section).
Figure 17:
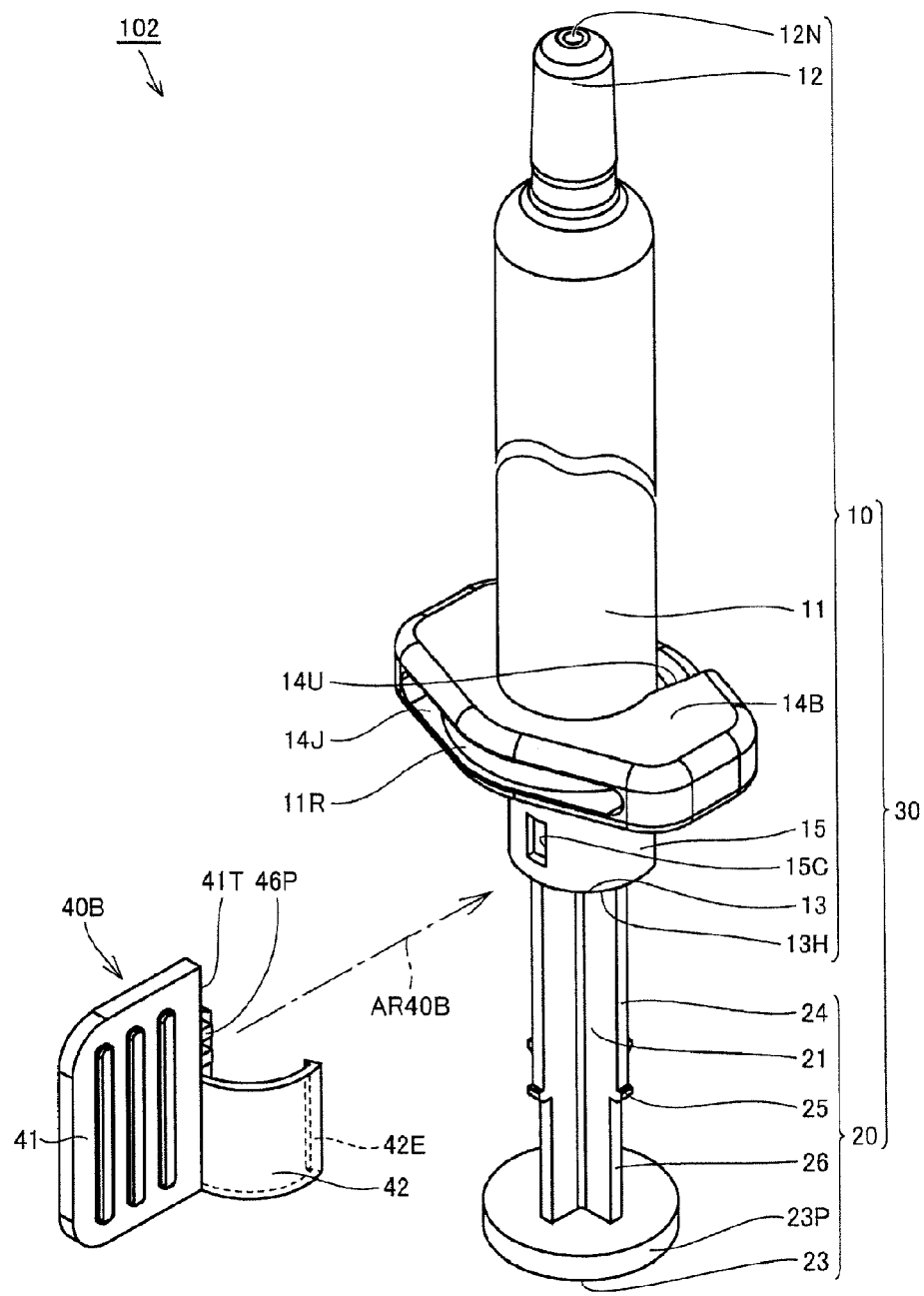
FIG. 17 is a second perspective view showing a state where the nasal cavity administration container according to the third embodiment has been disassembled partly (a plunger moving amount regulation member has been detached from the body section).
Figure 18:
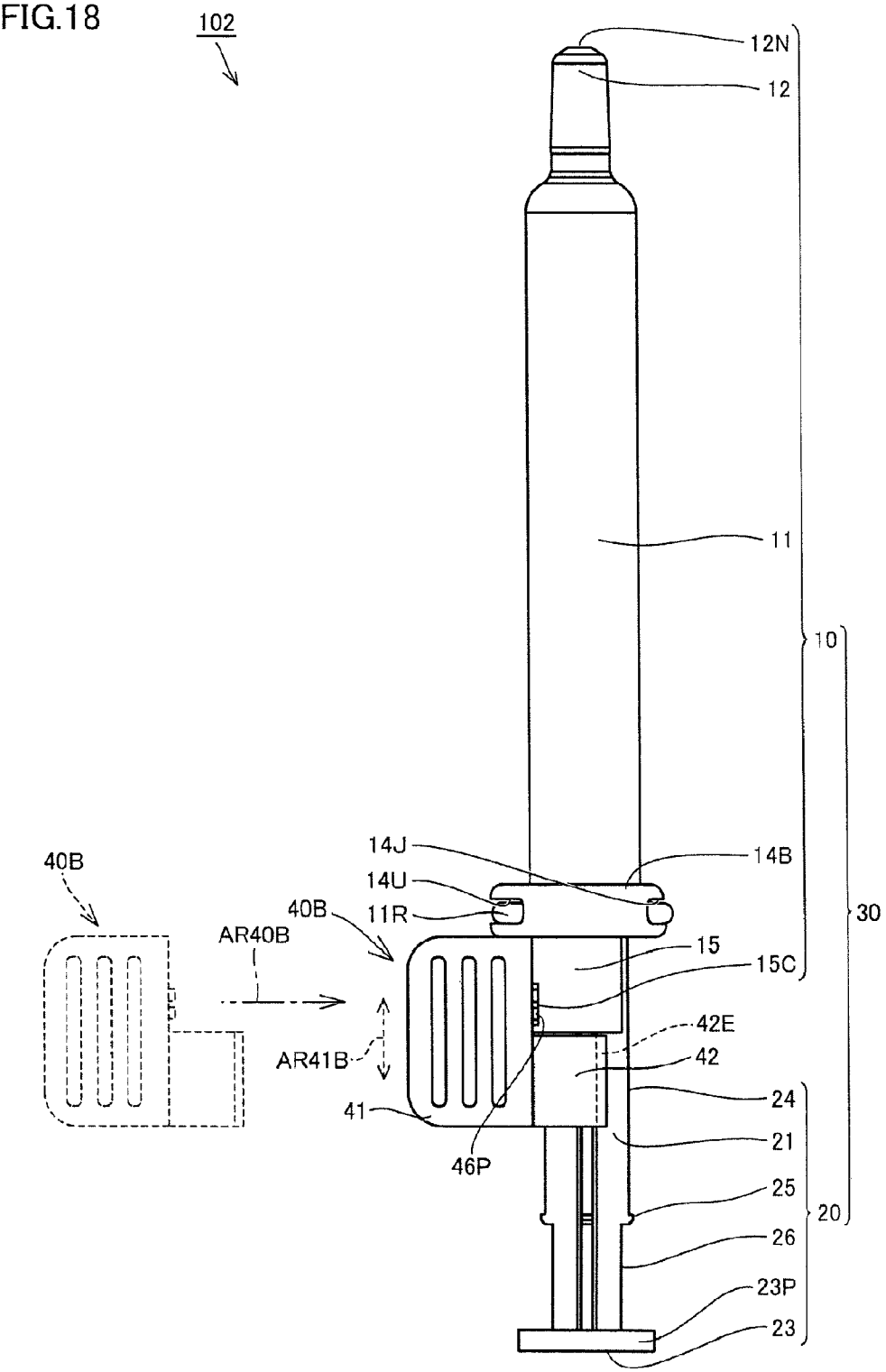
FIG. 18 is a side view showing the nasal cavity administration container according to the third embodiment.

Referring to FIGS. 16 to 18, a nasal cavity administration container 102 according to the present embodiment will be described. Nasal cavity administration container 102 differs from nasal cavity administration container 100 (see FIG. 1) according to the above-described first embodiment in the following points.

FIG. 16 is a first perspective view showing a state where nasal cavity administration container 102 has been disassembled partly (a plunger moving amount regulation member 40B has been detached from body section 30). As shown in FIG. 16, nasal cavity administration container 102 is provided with body section 30 and plunger moving amount regulation member 40B. Body section 30 includes medical fluid storage section 10 and plunger 20.

FIG. 17 is a second perspective view showing a state where nasal cavity administration container 102 has been disassembled partly (plunger moving amount regulation member 40B has been detached from body section 30). As shown in FIG. 17, medical fluid storage section 10 according to the present embodiment includes a finger clip part 14B. A recess 15C (first fitted part) is provided on the outer circumference of suspended part 15 of finger clip part 14B.

Plunger moving amount regulation member 40B according to the present embodiment is provided with a projection 46P (second fitted part) corresponding to the shape of recess 15C provided in suspended part 15, on an end face 41T of grip 41.

FIG. 18 is a side view showing nasal cavity administration container 102. As shown in FIG. 18, plunger moving amount regulation member 40B is attached to body section 30 (see arrow AR40B). In this state, recess 15C and projection 46P are fitted to each other. This fit regulates the movement of plunger moving amount regulation member 40B relative to body section 30 in the direction of arrow AR41B.

It is noted that plunger moving amount regulation member 40B may be attached to body section 30 with abutting part 25 of plunger 20 abutting on the other end 13 of suspended part 15, similarly to the above-described first embodiment. In this case, recess 15C and projection 46P are fitted to each other by attaching plunger moving amount regulation member 40B to body section 30. After recess 15C and projection 46P are fitted to each other, plunger 20 is moved away from medical fluid storage section 10. By such assembly, the state shown in FIG. 18 can also be obtained.

Plunger moving amount regulation member 40B and finger clip part 14B may be previously assembled to each other before finger clip part 14B is attached to flange part 11R. With plunger moving amount regulation member 40B and finger clip part 14B integrated together, plunger moving amount regulation member 40B and finger clip part 14B can be easily attached to barrel 11 (flange part 11R).

In nasal cavity administration container 102, the first administration and the second administration are each carried out similarly to the above-described first embodiment. At the time of the first administration, the movement of plunger moving amount regulation member 40B relative to body section 30 in the direction of arrow AR41B (see FIG. 18) is regulated. Since plunger moving amount regulation member 40B is fixed relative to body section 30 similarly to the above-described second embodiment, nasal cavity administration container 102 presents excellent operational stability when pushing plunger 20 into medical fluid storage section 10.

Fourth Embodiment

Figure 19:
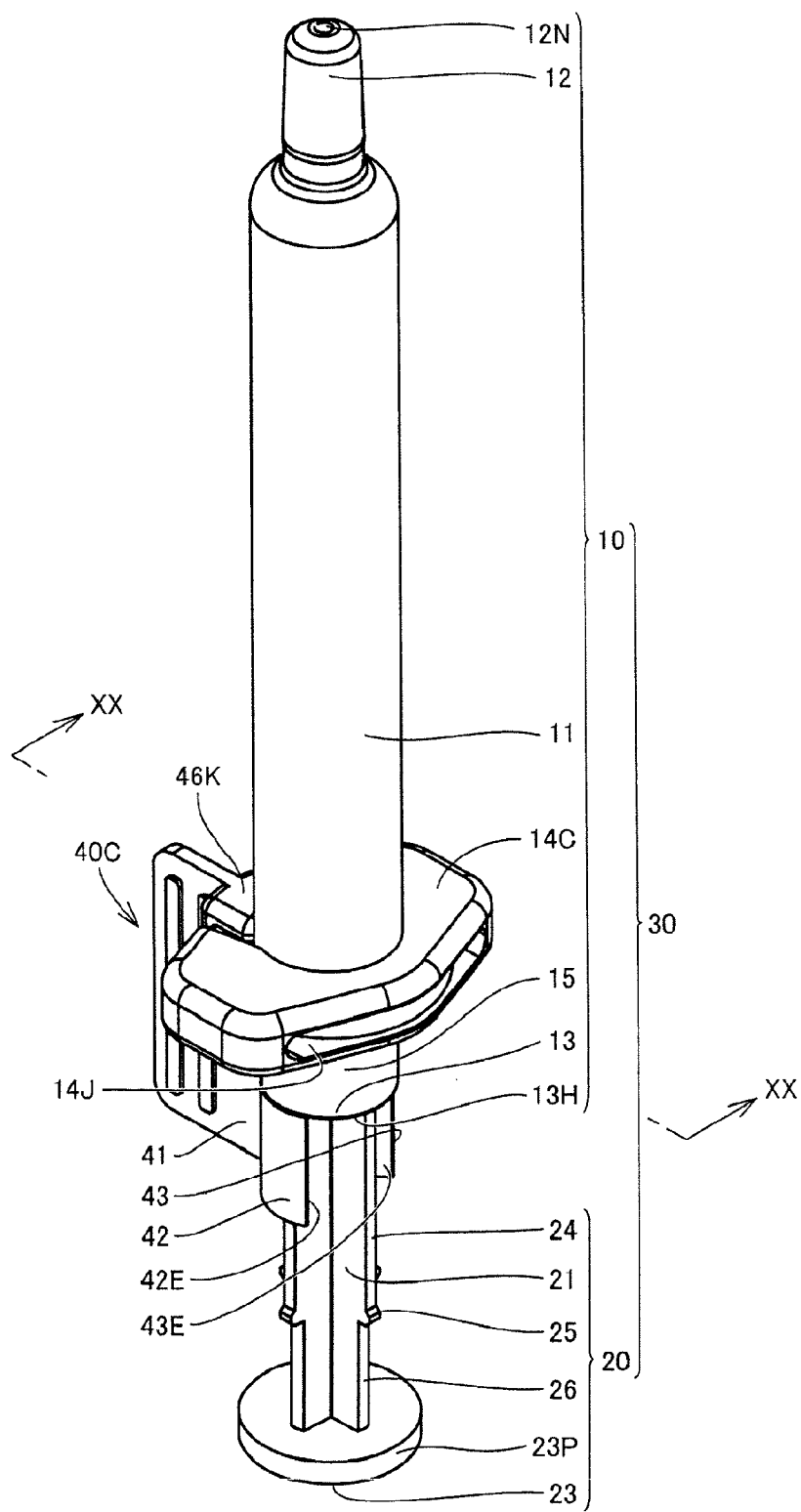
FIG. 19 is a perspective view showing a nasal cavity administration container according to a fourth embodiment.
Figure 20:
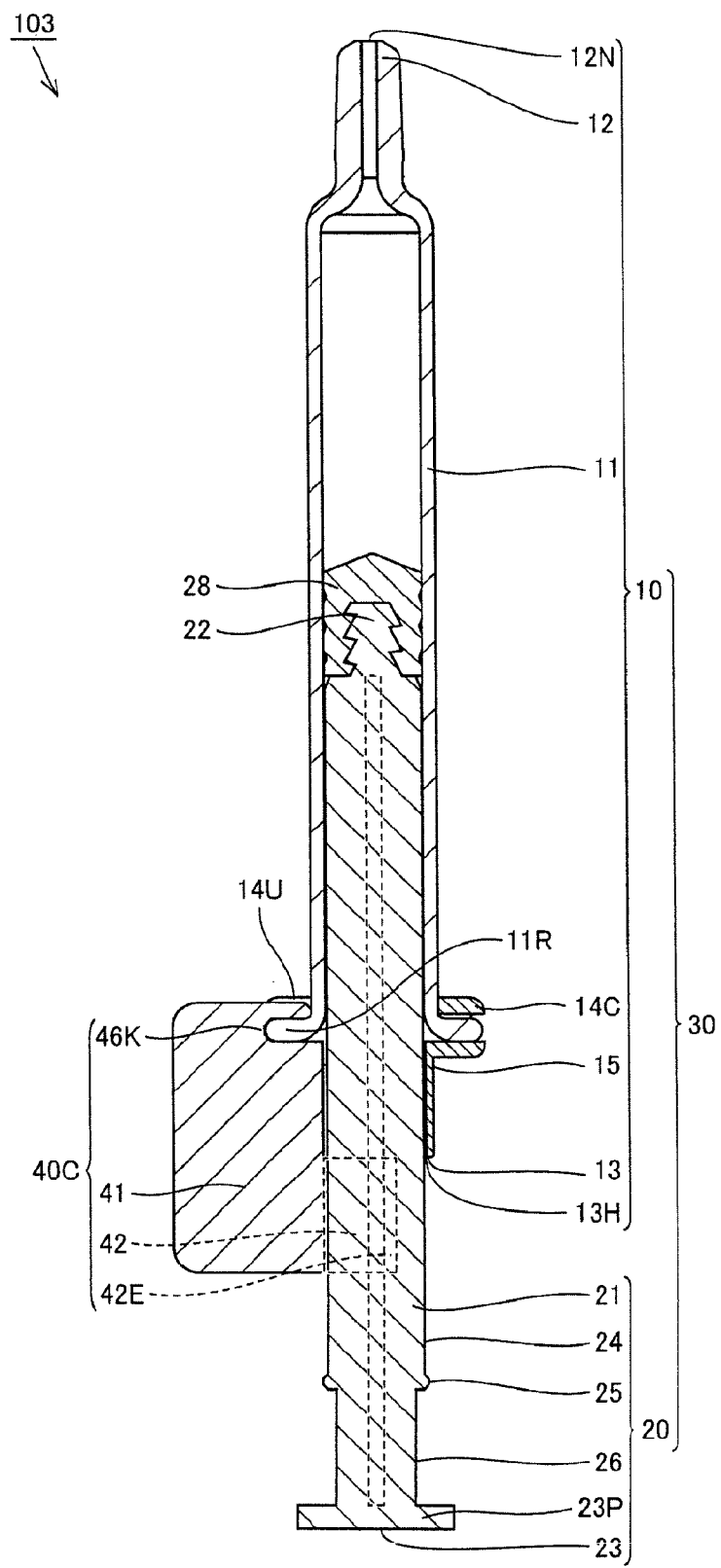
FIG. 20 is an arrow cross sectional view taken along the line XX-XX in FIG. 19.
Figure 21:
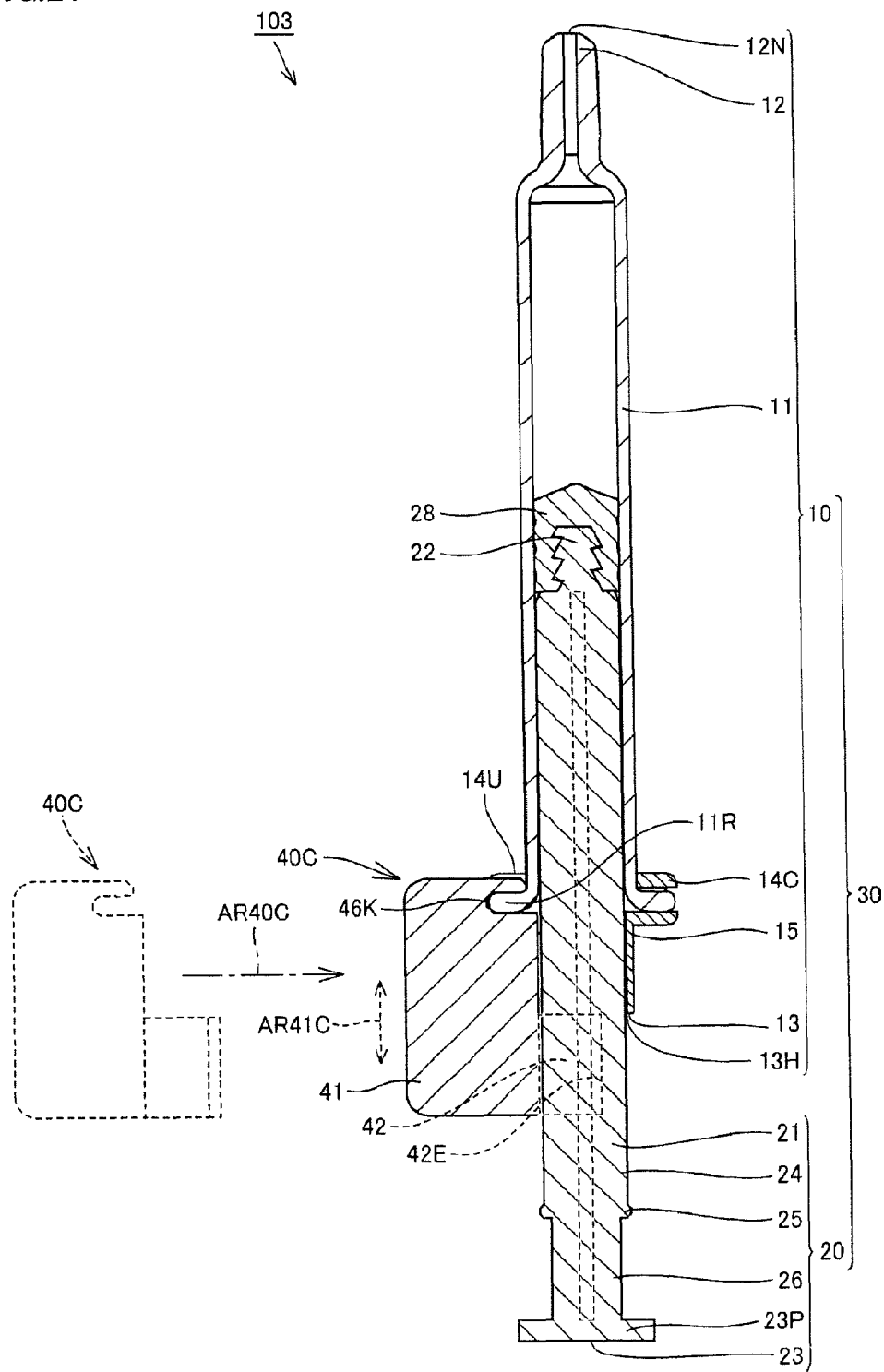
FIG. 21 is a cross sectional view showing how to assemble the nasal cavity administration container according to the fourth embodiment.

Referring to FIGS. 19 to 21, a nasal cavity administration container 103 according to the present embodiment will be described. Nasal cavity administration container 103 differs from nasal cavity administration container 100 (see FIG. 1) according to the above-described first embodiment in the following points.

FIG. 19 is a perspective view showing nasal cavity administration container 103. As shown in FIG. 19, nasal cavity administration container 103 is provided with body section 30 and a plunger moving amount regulation member 40C. Body section 30 includes medical fluid storage section 10 and plunger 20.

FIG. 20 is an arrow cross sectional view taken along the line XX-XX in FIG. 19. As shown in FIG. 20, medical fluid storage section 10 according to the present embodiment includes a finger clip part 14C. Notch 14U of finger clip part 14C is formed by cutting away so as to expose the circumference of flange part 11R. According to the present embodiment, flange part 11R implements the first fitted part.

Plunger moving amount regulation member 40C according to the present embodiment has a recess 46K (second fitted part) corresponding to the shape of flange part 11R. With plunger moving amount regulation member 40C attached to body section 30, recess 46K is fitted over flange part 11R.

FIG. 21 is a cross sectional view showing nasal cavity administration container 103 and shows how to assemble nasal cavity administration container 103. As shown in FIG. 21, plunger moving amount regulation member 40C is attached to body section 30 (see arrow AR40C). By attaching plunger moving amount regulation member 40C to body section 30, recess 46K and flange part 11R are fitted to each other. This fit regulates the movement of plunger moving amount regulation member 40C in the direction of arrow AR41C relative to body section 30.

It is noted that plunger moving amount regulation member 40C may be attached to body section 30 with abutting part 25 of plunger 20 abutting on the other end 13 of suspended part 15, similarly to the above-described first embodiment. In this case, recess 46K and flange part 11R are fitted to each other by attaching plunger moving amount regulation member 40C to body section 30. After recess 46K and flange part 11R are fitted to each other, plunger 20 is moved away from medical fluid storage section 10. By such assembly, the state shown in FIG. 18 can also be obtained.

Plunger moving amount regulation member 40C and finger clip part 14C may be previously assembled to each other before finger clip part 14C is attached to flange part 11R. With plunger moving amount regulation member 40C and finger clip part 14C integrated together, plunger moving amount regulation member 40C and finger clip part 14C can be easily attached to barrel 11 (flange part 11R).

In nasal cavity administration container 103, the first administration and the second administration are each carried out similarly to the above-described first embodiment. At the time of the first administration, the movement of plunger moving amount regulation member 40C relative to body section 30 in the direction of arrow AR41C (see FIG. 21) is regulated. Since plunger moving amount regulation member 40C is fixed relative to body section 30 similarly to the above-described second and third embodiments, nasal cavity administration container 103 presents excellent operational stability when pushing plunger 20 into medical fluid storage section 10.

Fifth Embodiment

Structure of Nasal Cavity Administration Container 104

Figure 22:
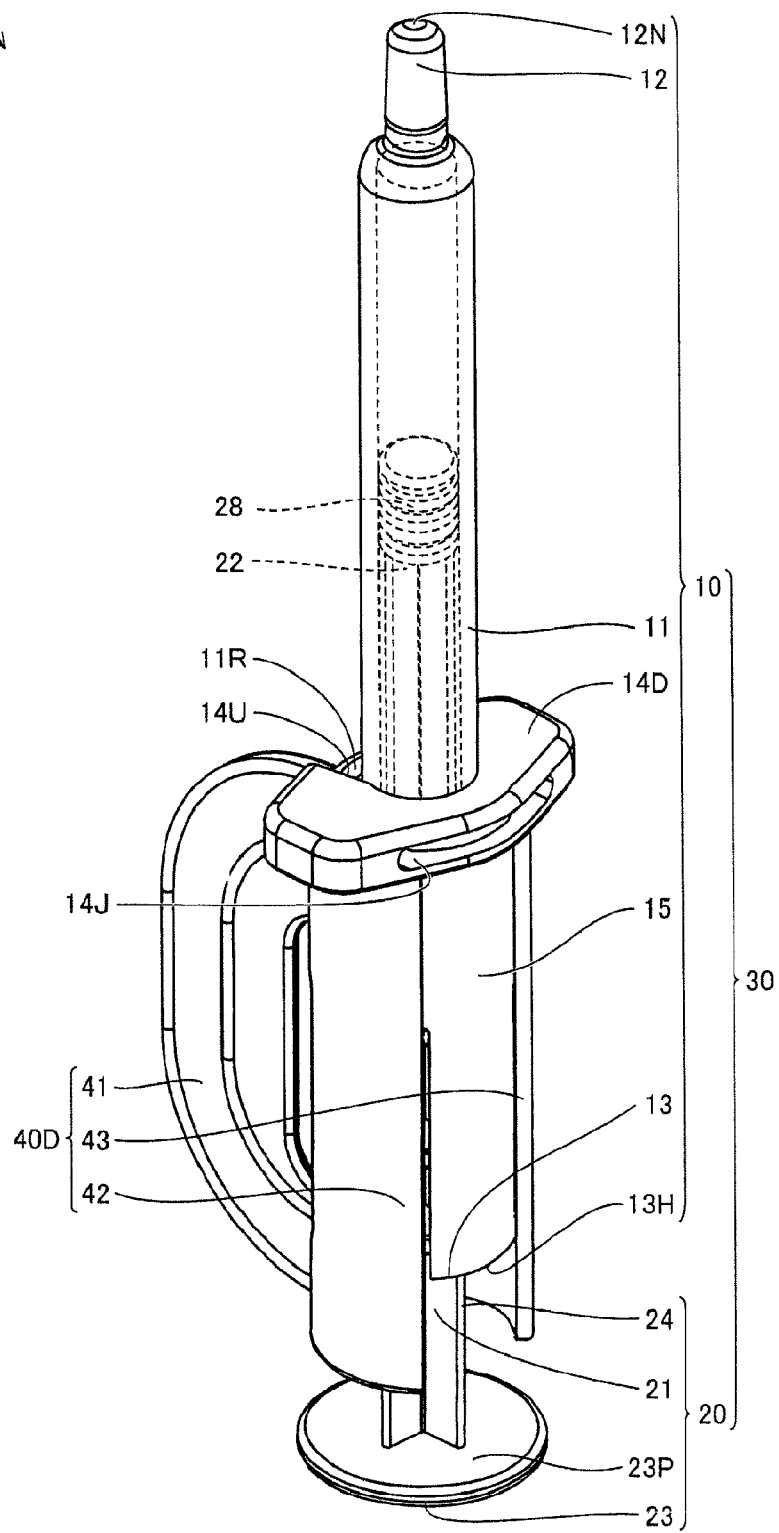
FIG. 22 is a first perspective view showing a nasal cavity administration container according to a fifth embodiment.
Figure 23:
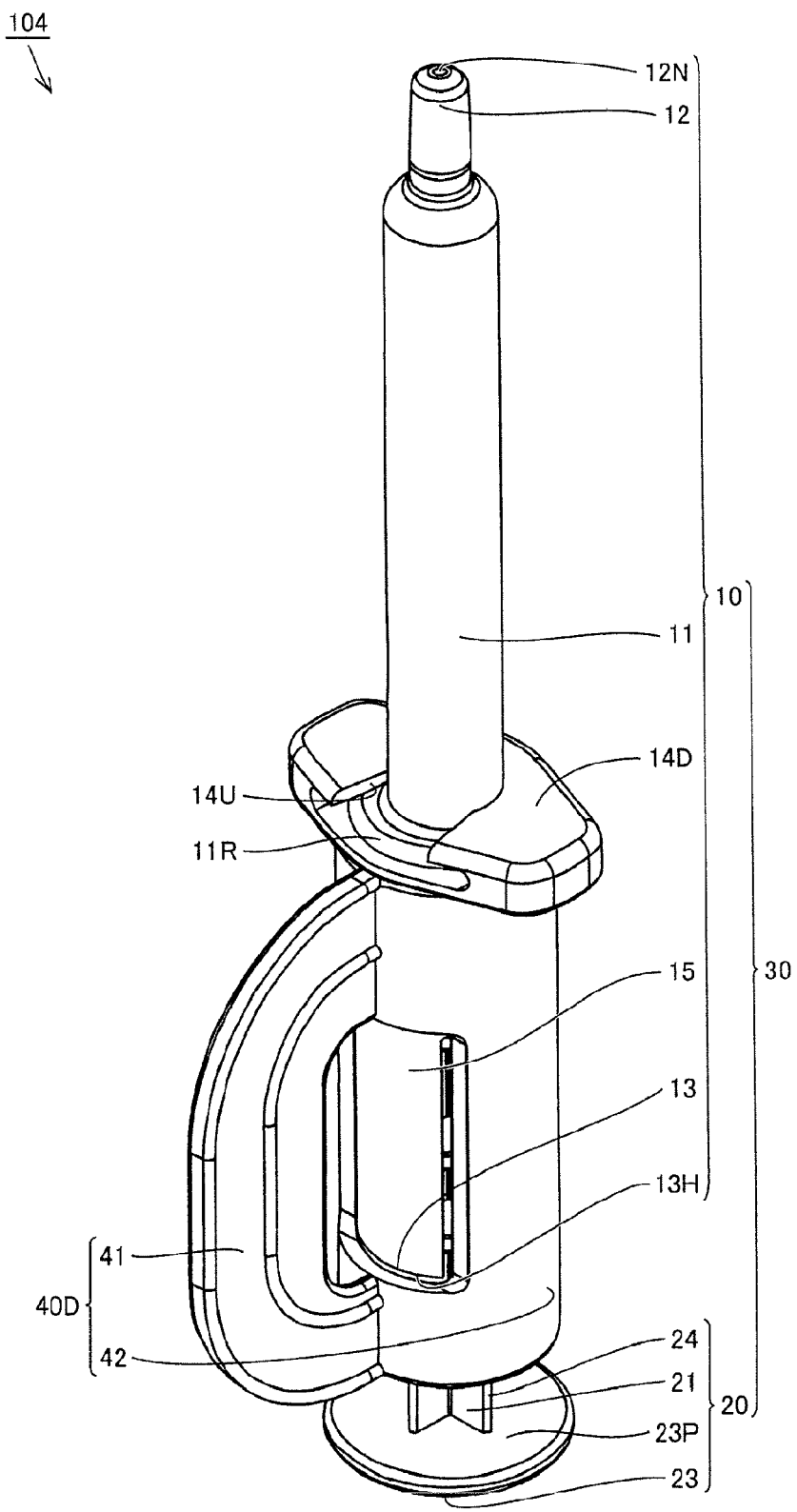
FIG. 23 is a second perspective view showing the nasal cavity administration container according to the fifth embodiment.

Referring to FIGS. 22 to 27, the structure of a nasal cavity administration container 104 according to the present embodiment will be described. FIG. 22 is a first perspective view showing nasal cavity administration container 104. FIG. 23 is a second perspective view showing nasal cavity administration container 104.

As shown in FIGS. 22 and 23, nasal cavity administration container 104 is provided with body section 30 and a plunger moving amount regulation member 40D. Body section 30 includes medical fluid storage section 10 and plunger 20.

Medical Fluid Storage Section 10

Medical fluid storage section 10 is composed of barrel 11 and a finger clip part 14D. Barrel 11 has a substantially cylindrical hollow shape. Plunger 20 and gasket 28 which will be described later are inserted into barrel 11. One end of barrel 11 constitutes one end 12 of medical fluid storage section 10. Nozzle 12N is formed on the one end 12 side of medical fluid storage section 10. Spray nozzle 12M (see FIG. 1) communicating with the inside of barrel 11 by way of nozzle 12N is attached to the one end 12 side of medical fluid storage section 10. Barrel 11 and spray nozzle 12M may be formed integrally, or may be formed as separate units and then attached to each other as in the present embodiment.

Figure 24:
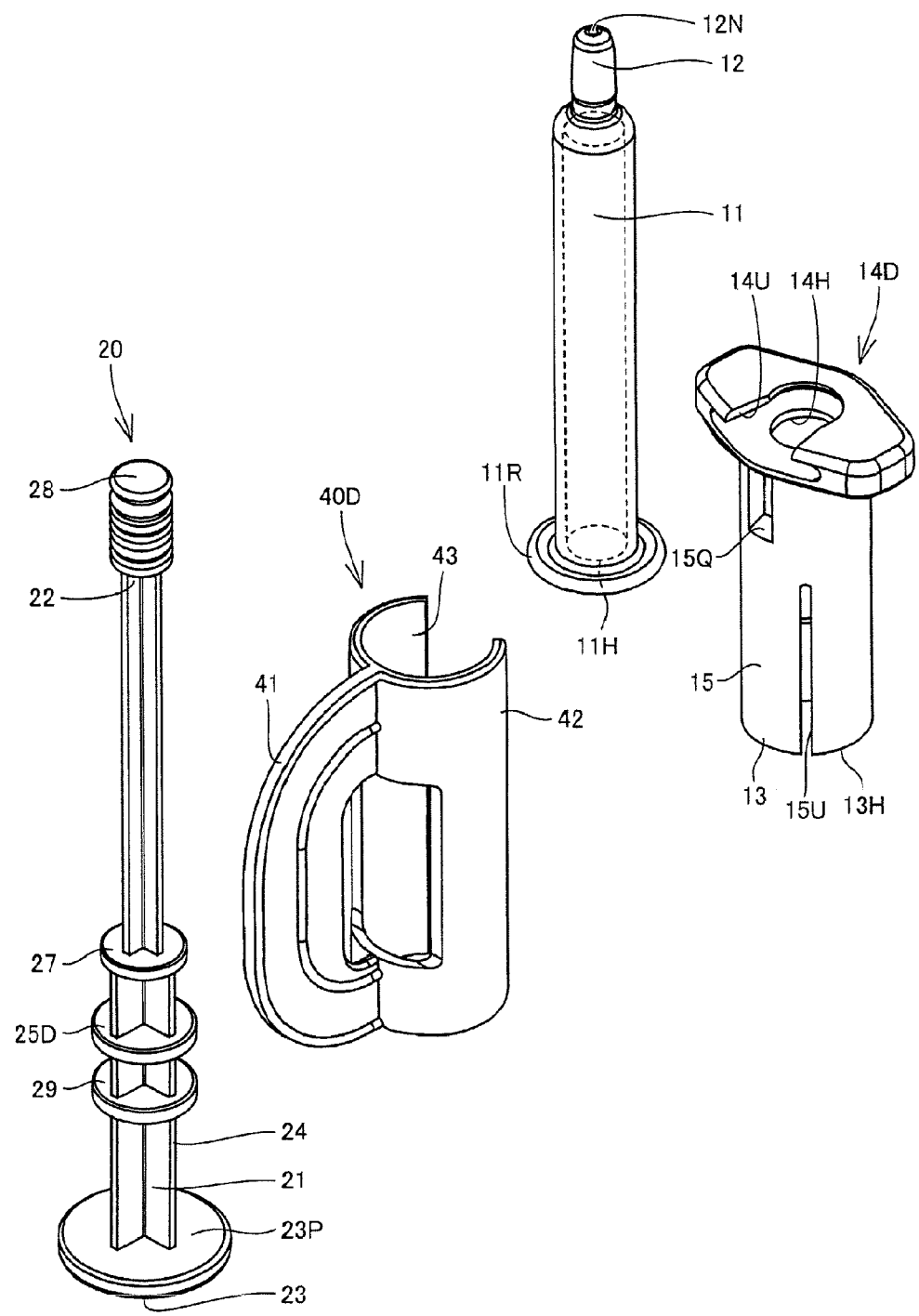
FIG. 24 is a perspective view showing a state where the nasal cavity administration container according to the fifth embodiment has been disassembled.

FIG. 24 is a perspective view showing a state where nasal cavity administration container 104 has been disassembled. Similarly to the above-described first embodiment, flange part 11R bulging outwardly in the cylinder radial direction is provided on the other end side of barrel 11. Opening 11H communicating with the inside of barrel 11 is formed on the inner side of flange part 11R.

Notch 14U corresponding to the shape of flange part 11R is provided in finger clip part 14D. Notch 14U communicates with an opening 14J (see FIG. 22) extending through toward the outer edge of finger clip part 14D. Finger clip part 14D is attached to flange part 11R by frictional engagement while grasping flange part 11R.

Opening 14H through which plunger 20 and gasket 28 pass is also provided in finger clip part 14D. Suspended part 15 is provided to hang down continuously with opening 14H. Suspended part 15 has a cylindrical shape. The leading end of suspended part 15 in the direction of hanging down constitutes the other end 13 of medical fluid storage section 10 (see FIG. 22). Opening 13H through which plunger 20 and gasket 28 pass is formed on the other end 13 side of medical fluid storage section 10.

Figure 25:
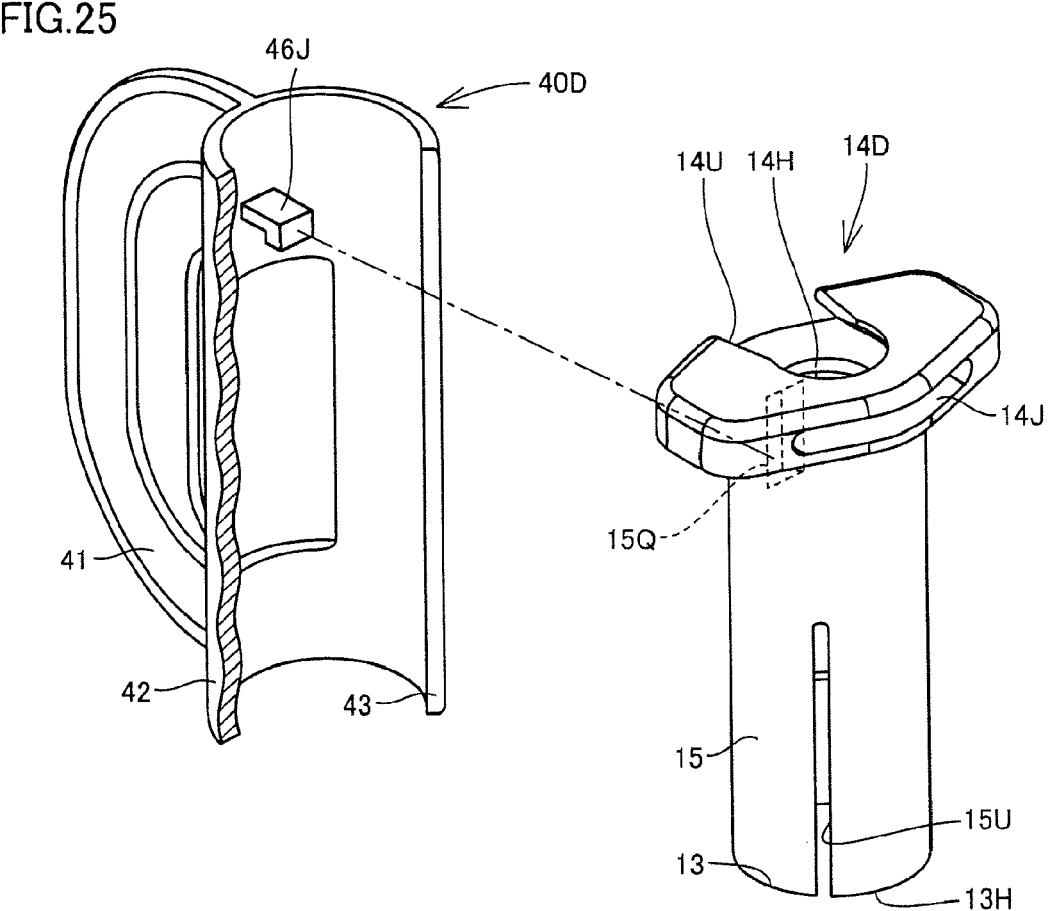
FIG. 25 is a perspective view showing how to assemble a plunger moving amount regulation member and a finger clip part provided for the nasal cavity administration container according to the fifth embodiment to each other.

FIG. 25 is a perspective view showing how to assemble plunger moving amount regulation member 40D and finger clip part 14D provided for nasal cavity administration container 104 to each other. As shown in FIG. 25, suspended part 15 according to the present embodiment is provided with four notches 15U extending in the longitudinal direction of suspended part 15. Four notches 15U are arranged at 90° intervals (see FIG. 26). By providing notches 15U in suspended part 15, the end side (the other end 13 side) of suspended part 15 can be elastically deformed like a plate spring.

Suspended part 15 is also provided with an opening 15Q (also see FIG. 24). Opening 15Q corresponds to the shape of a hook part 46J of plunger moving amount regulation member 40D which will be described later. A folded portion 15V (see FIG. 27) is provided on the inner side of opening 15Q. Folded portion 15V is provided to be bent toward the inner diameter side of suspended part 15 and is inclined toward opening 15Q.

Figure 26:
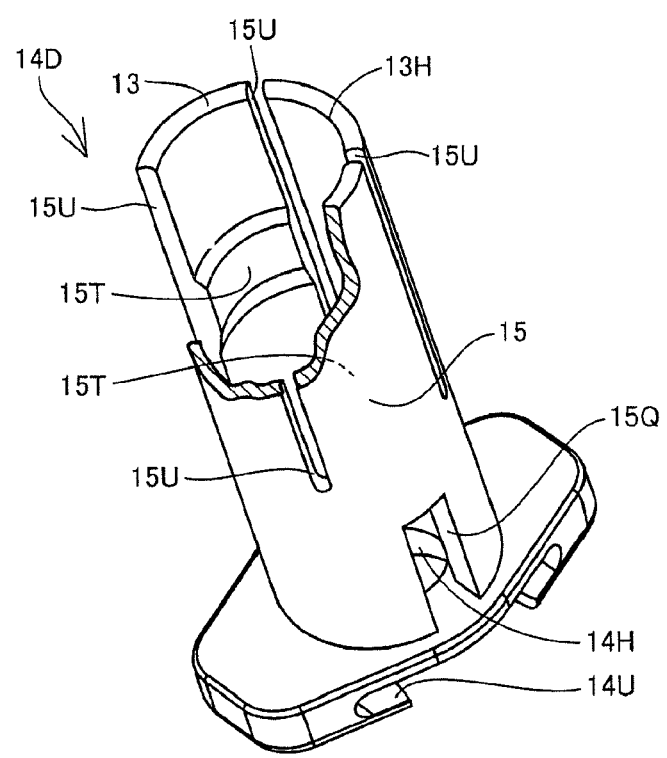
FIG. 26 is a perspective view showing the finger clip part provided for the nasal cavity administration container according to the fifth embodiment.

FIG. 26 is a perspective view showing finger clip part 14D provided for nasal cavity administration container 104. By providing notches 15U in suspended part 15, the end side (the other end 13 side) of suspended part 15 is divided into four sections. Projections 15T (also see FIG. 27) having a substantially trapezoidal sectional shape are provided on two sections opposed to each other among the sections on the end side (the other end 13 side) of suspended part 15 divided into four.

Plunger 20

Referring again to FIG. 24, plunger 20 according to the present embodiment has a substantially rod-like shape. Plunger 20 has four ribs 21 having a thin plate shape. Four ribs 21 extend in the longitudinal direction of plunger 20 from one end 22 toward the other end 23 of plunger 20. Four ribs 21 are arranged at 90° intervals, and stand up toward the outside perpendicularly to the longitudinal direction of plunger 20.

Gasket 28 made of rubber is provided on one end 22 of plunger 20. Disc-like pressing part 23P is provided on the other end 23 of plunger 20. As described above, plunger 20 is inserted into medical fluid storage section 10 (barrel 11) together with gasket 28 from the one end 22 side through opening 13H of medical fluid storage section 10 (barrel 11).

Plunger 20 according to the present embodiment is provided with an abutting part 27 (first abutting part), an abutting part 25D (second abutting part) and an abutting part 29. Abutting part 27 has a disc-like shape. It is noted that abutting parts 25D and 29 may be provided according to necessity. When abutting parts 25D and 29 are provided for plunger 20, abutting parts 25D and 29 both have a disc-like shape. Abutting part 27 is formed to have a diameter smaller than abutting parts 25D and 29. Abutting parts 25D and 29 are formed to have the same diameter. Abutting parts 27, 25D and 29 are arranged in this order from the one end 22 side toward the other end 23 side of plunger 20, and are spaced from each other. Abutting parts 27, 25D and 29 will be described later in further details.

Plunger Moving Amount Regulation Member 40D

Referring again to FIGS. 24 and 25, plunger moving amount regulation member 40D includes grip 41, stoppers 42, 43 and hook part 46J (see FIG. 25). Stoppers 42 and 43 are formed continuously with the end of grip 41. Stoppers 42 and 43 are symmetrically formed on the opposite sides of grip 41, and present a substantially halved cylindrical shape as a whole.

As shown in FIG. 25, hook part 46J is provided to project in the form of the letter L on the inner circumferential surface of stoppers 42 and 43 presenting a substantially halved cylindrical shape. As described above, the shape of hook part 46J corresponds to the shape (of folded portion 15V) of opening 15Q provided in suspended part 15 of finger clip part 14D. With nasal cavity administration container 104 assembled (see FIGS. 22 and 23), hook part 46J is engaged with folded portion 15V (see FIG. 27) provided continuously with opening 15Q.

Assembly of Nasal Cavity Administration Container 104

Figure 27:
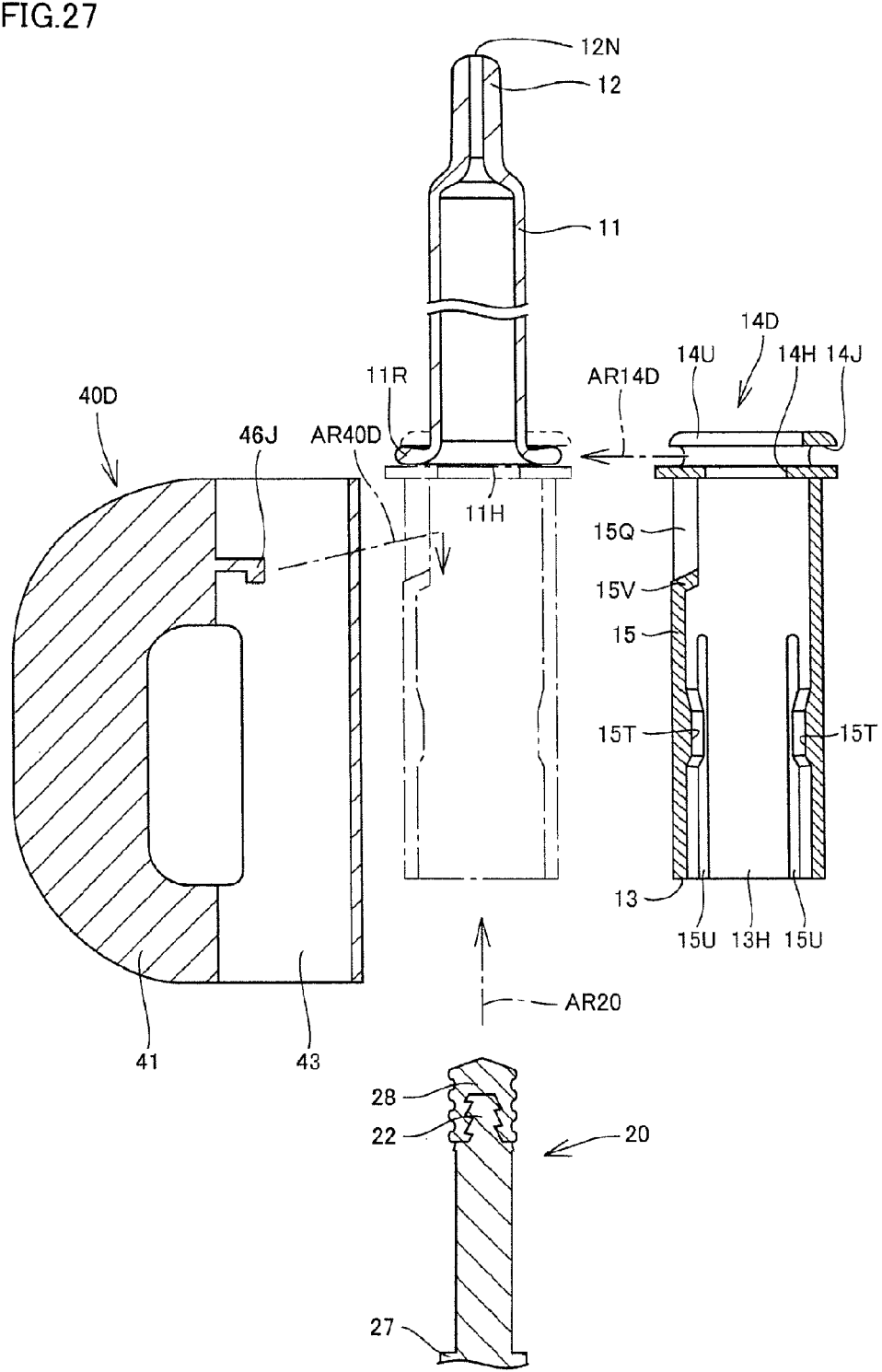
FIG. 27 is a cross sectional view showing how to assemble the nasal cavity administration container according to the fifth embodiment.

FIG. 27 is a cross sectional view showing how to assemble nasal cavity administration container 104. When nasal cavity administration container 104 is assembled, finger clip part 14D is first attached to flange part 11R of barrel 11 (see arrow AR14D). As described above, finger clip part 14D is attached to flange part 11R by frictional engagement while grasping flange part 11R. Medical fluid storage section 10 (see FIGS. 22 and 23) is thereby obtained. Moreover, as described above, spray nozzle 12M (see FIG. 1) is attached to one end 12 of barrel 11.

Next, stoppers 42 and 43 of plunger moving amount regulation member 40D are attached so as to surround the outer circumference of finger clip part 14D. Hook part 46J of plunger moving amount regulation member 40D is inserted into opening 15Q (folded portion 15V) of finger clip part 14D so as to be engaged with opening 15Q (see arrow AR40D).

Then, plunger 20 with gasket 28 attached to one end 22 is prepared. Gasket 28 and plunger 20 are inserted into barrel 11 (see arrow AR20) through opening 13H on the other end 13 of medical fluid storage section 10 and opening 11H of barrel 11. Body section 30 (see FIGS. 22 and 23) including medical fluid storage section 10 and plunger 20 is thereby obtained.

Figure 28:
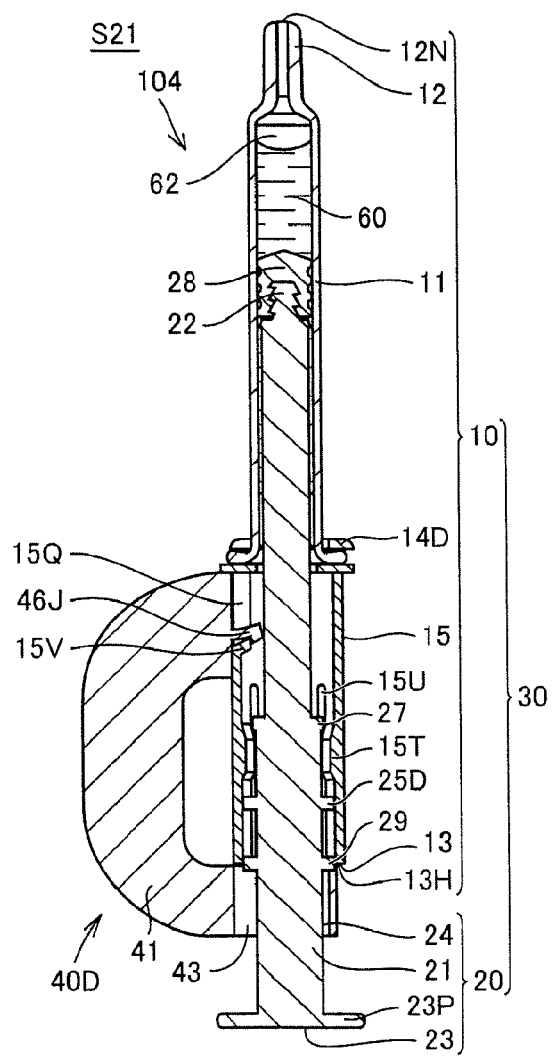
FIG. 28 is a cross sectional view showing a first administration preparatory state of the nasal cavity administration container according to the fifth embodiment.

With nasal cavity administration container 104 assembled, plunger moving amount regulation member 40D is engaged with body section 30 (specifically, opening 15Q and folded portion 15V of finger clip part 14D) by means of hook part 46J (see FIG. 28). Abutting part 27 of plunger 20 is arranged to be opposed to the leading end of hook part 46J provided for plunger moving amount regulation member 40D (see FIG. 28). Abutting part 25D of plunger 20 is arranged to be opposed to projections 15T provided on finger clip part 14D (see FIG. 28).

As will be described later in detail with reference to FIG. 30, this structure allows the state where plunger moving amount regulation member 40D is engaged with body section 30 to be relieved only in the state where pressing part 23P of plunger 20 abuts on stoppers 42 and 43 of plunger moving amount regulation member 40D (the state shown in FIG. 30).

Operation of Nasal Cavity Administration Container 104

Referring to FIGS. 28 to 33, the operation of nasal cavity administration container 104 will be described. Nasal cavity administration container 104 sequentially transitions among the respective states of a first administration preparatory state S21 (see FIG. 28), a first administration start state S22 (see FIG. 29), a first administration completion state S23 (see FIG. 30), a second administration preparatory state S24 (see FIG. 31), a second administration start state S25 (see FIG. 32), and a second administration completion state S26 (see FIG. 33).

As will be described later in detail, a first administration of medical fluid 60 is carried out through first administration preparatory state S21, first administration start state S22 and first administration completion state S23. A second administration of medical fluid 60 is carried out through second administration preparatory state S24, second administration start state S25 and second administration completion state S26.

First Administration Preparatory State S21

Referring to FIG. 28, medical fluid 60 is injected (or sucked) into nasal cavity administration container 104 as assembled from the nozzle 12N side (the state shown in FIG. 28). When injection of medical fluid 60 is completed, nasal cavity administration container 104 transitions to first administration preparatory state S21. In this occasion, air 62 may enter medical fluid storage section 10 (barrel 11) on the one end 12 side.

First Administration Start State S22

Figure 29:
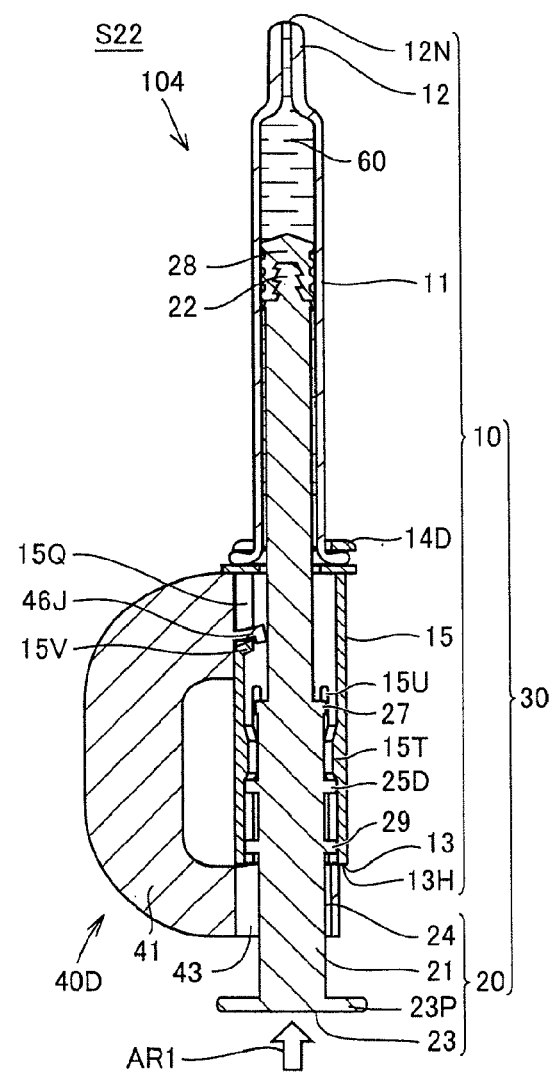
FIG. 29 is a cross sectional view showing a first administration start state of the nasal cavity administration container according to the fifth embodiment.

Referring to FIG. 29, the operation called priming is carried out for the purpose of setting the dose of medical fluid 60 to be administered to a nasal cavity at a predetermined value and exhausting air having entered medical fluid storage section 10 (barrel 11) (according to necessity).

Specifically, plunger 20 is inserted into medical fluid storage section 10 (barrel 11) (see arrow AR1). Plunger 20 and gasket 28 enter barrel 11 while in sliding contact with the inside of barrel 11 until abutting part 25D of plunger 20 abuts on projections 15T (the rear ends of projections 15T) of finger clip part 14D.

When abutting part 25D of plunger 20 abuts on projections 15T of finger clip part 14D, the movement of plunger moving amount regulation member 40D relative to body section 30 is stopped (the state shown in FIG. 29). According to the present embodiment, finger clip part 14D constituting body section 30 corresponds to "one of stoppers 42, 43 and body section 30."

When the movement of plunger moving amount regulation member 40 relative to body section 30 is stopped, nasal cavity administration container 104 transitions to first administration start state S22. The air in medical fluid storage section 10 (barrel 11) is forced out of medical fluid storage section 10, and the dose of medical fluid 60 to be administered to a nasal cavity is set at the predetermined value (priming is carried out).

First Administration Completion State S23

Figure 30:
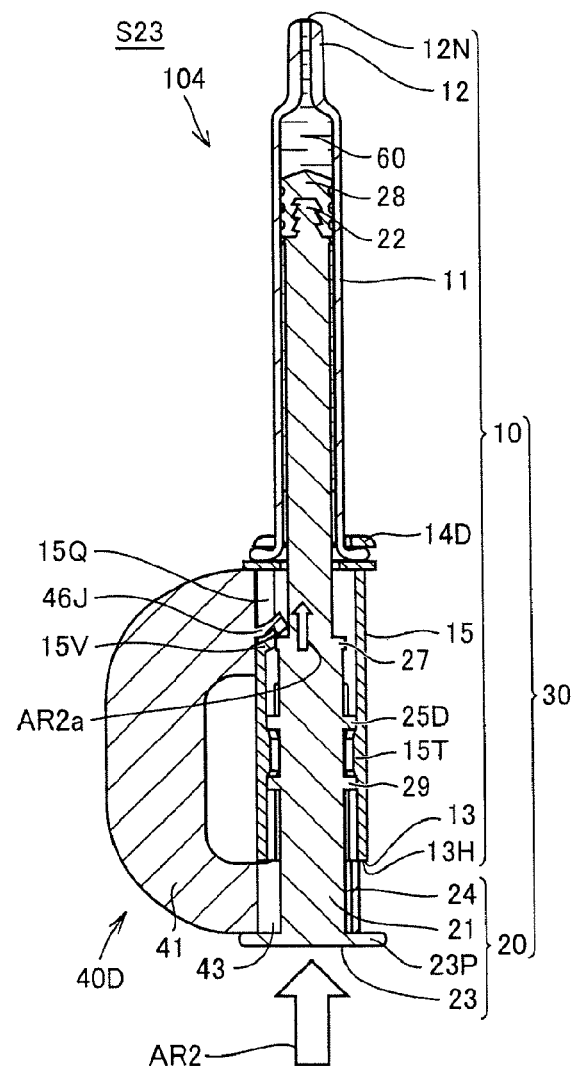
FIG. 30 is a cross sectional view showing a first administration completion state of the nasal cavity administration container according to the fifth embodiment.

Referring to FIG. 30, after the dose of medical fluid 60 to be administered to a nasal cavity is set at the predetermined value, spray nozzle 12M (see FIG. 1) attached to the nozzle 12N side is located in one of the nasal cavities. In this state, plunger 20 is strongly pushed into medical fluid storage section 10 (barrel 11) by means of pressing part 23P (see arrow AR2).

By vigorously pushing plunger 20, the state where abutting part 25 of plunger 20 abuts on projections 15T of finger clip part 14D is relieved.

Abutting part 25D of plunger 20 may be formed to come into frictional engagement with the inner circumferential surface of projections 15T at the start of the first administration of medical fluid 60. This structure is obtained by slightly increasing the projecting dimension of abutting part 25D with respect to the inner diameter of projections 15T.

With this structure, at the start of the first administration, relatively large compressive force is applied to pressing part 23P so as to relieve the frictional engagement of abutting part 25 with projections 15T of abutting part 25D. After the frictional engagement is relieved by the relatively large compressive force, plunger 20 can be vigorously pushed into medical fluid storage section 10. Medical fluid 60 can be appropriately administered in a favorable mist form in the first administration.

Plunger 20 moves forward inside medical fluid storage section 10 while abutting part 25D entering toward the inner side relative to projections 15T. In this occasion, suspended part 15 divided into four by providing notches 15U is slightly elastically deformed to the outside. Gasket 28 is pushed by plunger 20, thereby entering medical fluid storage section 10.

In this manner, medical fluid 60 in medical fluid storage section 10 is sprayed through spray nozzle 12M (see FIG. 1) by the movement of gasket 28. A mist of medical fluid 60 is administered to one of the nasal cavities through spray nozzle 12M. Plunger 20 moves forward until pressing part 23P abuts on the lower ends of stoppers 42, 43 of plunger moving amount regulation member 40D.

When pressing part 23P abuts on the lower ends of stoppers 42, 43 of plunger moving amount regulation member 40D, the movement of plunger 20 relative to medical fluid storage section 10 is stopped (the state shown in FIG. 30). In this occasion, abutting part 29 abuts on the rear ends of projections 15T. When the movement of plunger 20 is stopped, the first administration is completed, and nasal cavity administration container 104 transitions to first administration completion state S23. The amount of stroke of plunger 20 relative to medical fluid storage section 10 defines the first dosage of medical fluid 60.

Here, as indicated by an arrow AR2a, abutting part 27 provided for plunger 20 abuts on hook part 46J of plunger moving amount regulation member 40D at the same time when pressing part 23P abuts on the lower ends of stoppers 42 and 43 of plunger moving amount regulation member 40D. Abutting part 27 of plunger 20 causes hook part 46J to be elastically deformed away from folded portion 15V such that the state where hook part 46J is engaged with opening 15Q and folded portion 15V is relieved.

By this elastic deformation, in the state where the first administration of medical fluid 60 has been completed (the state shown in FIG. 30), the state where hook part 46J is engaged with opening 15Q and folded portion 15V is relieved. In this manner, in nasal cavity administration container 104, the state where plunger moving amount regulation member 40D is engaged with body section 30 can be relieved only in the state where pressing part 23P of plunger 20 abuts on stoppers 42, 43 of plunger moving amount regulation member 40D (the state shown in FIG. 30).

Second Administration Preparatory State S24

Figure 31:
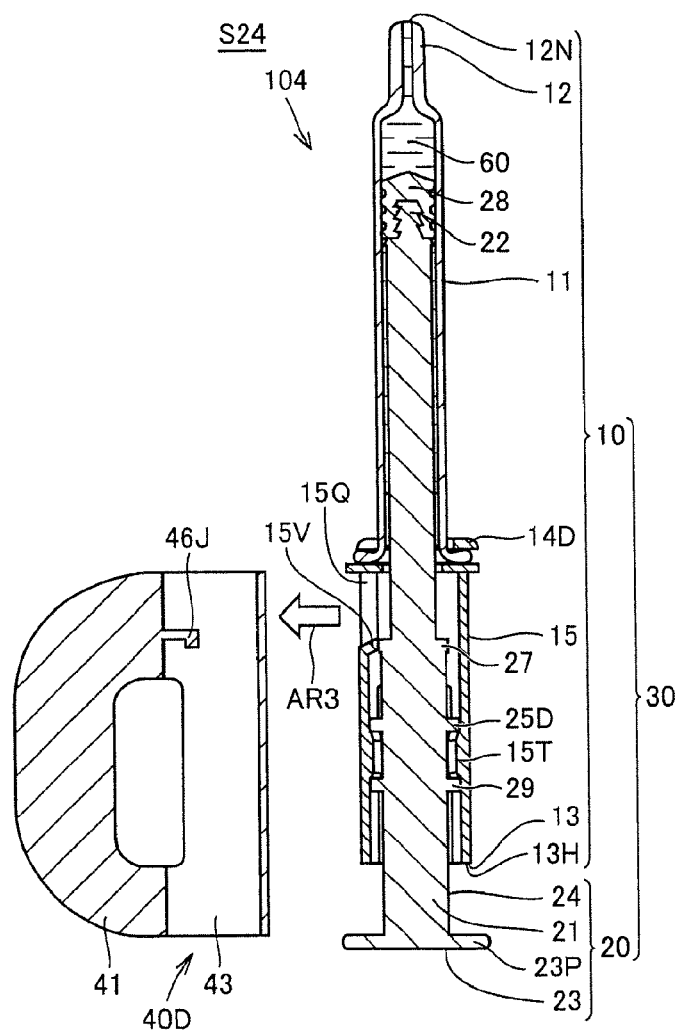
FIG. 31 is a cross sectional view showing a second administration preparatory state of the nasal cavity administration container according to the fifth embodiment.

Referring to FIG. 31, in order to carry out the second administration of medical fluid 60, plunger moving amount regulation member 40D is detached from body section 30 (the state shown in FIG. 31) as indicated by an arrow AR3. When plunger moving amount regulation member 40D is detached from body section 30, nasal cavity administration container 104 transitions to second administration preparatory state S24.

Second Administration Start State S25

Figure 32:
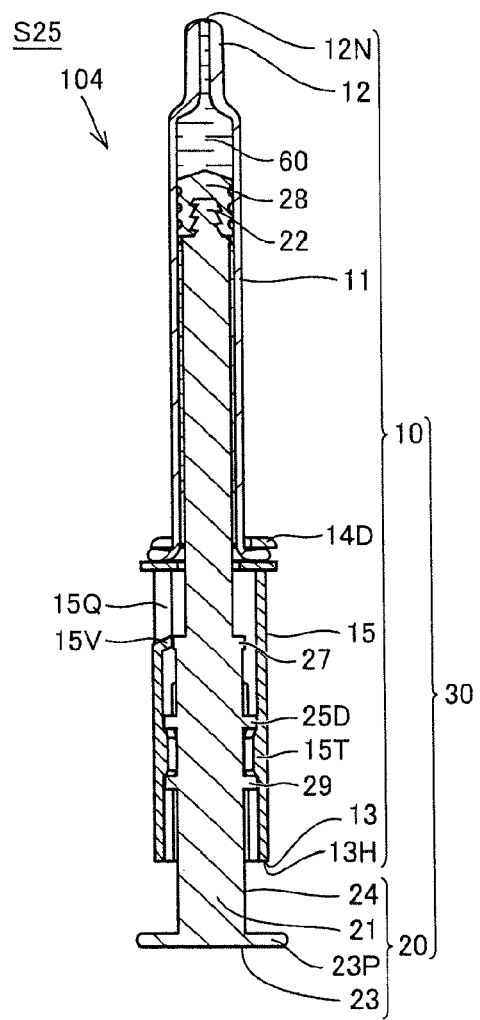
FIG. 32 is a cross sectional view showing a second administration start state of the nasal cavity administration container according to the fifth embodiment.

Referring to FIG. 32, after plunger moving amount regulation member 40D is detached from body section 30 (after second administration preparatory state S24), spray nozzle 12M (see FIG. 1) attached on the nozzle 12N side of nasal cavity administration container 104 is located in the other nasal cavity. Nasal cavity administration container 104 thereby transitions to second administration start state S25.

Second Administration Completion State S26

Figure 33:
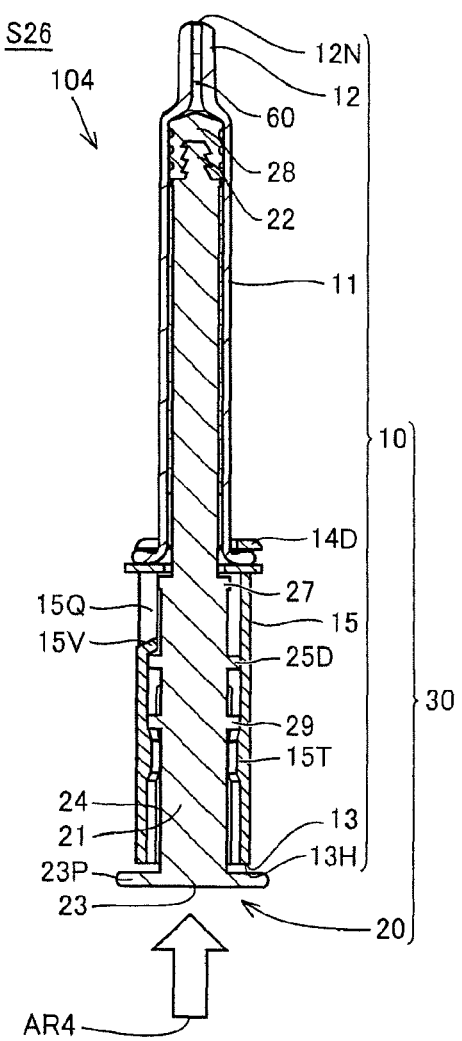
FIG. 33 is a cross sectional view showing a second administration completion state of the nasal cavity administration container according to the fifth embodiment.

Referring to FIG. 33, after spray nozzle 12M (see FIG. 1) of nasal cavity administration container 104 is located in the other nasal cavity, plunger 20 is further pushed into medical fluid storage section 10 (barrel 11) by means of pressing part 23P (see arrow AR4).

By vigorously pushing plunger 20, the state where abutting part 29 of plunger 20 abuts on projections 15T of finger clip part 14D is relieved. Plunger 20 moves forward inside medical fluid storage section 10. Gasket 28 is pushed by plunger 20, thereby further entering medical fluid storage section 10.

Abutting part 29 of plunger 20 may be formed to come into frictional engagement with the inner circumferential surface of projections 15T at the start of the second administration of medical fluid 60. This structure is obtained by slightly increasing the projecting dimension of abutting part 29 with respect to the inner diameter of projections 15T.

With this structure, at the start of the second administration, relatively large compressive force is applied to pressing part 23P so as to relieve the frictional engagement of abutting part 29 with projections 15T. After the frictional engagement is relieved by the relatively large compressive force, plunger 20 can be vigorously pushed into medical fluid storage section 10 by that force. Medical fluid 60 can also be appropriately administered in a favorable mist form in the second administration.

In this manner, medical fluid 60 in medical fluid storage section 10 is sprayed through spray nozzle 12M (see FIG. 1) by the movement of gasket 28. A mist of medical fluid 60 is administered to one of the nasal cavities through spray nozzle 12M. Plunger 20 moves forward until gasket 28 abuts on the upper end inside barrel 11. Plunger 20 may be formed so as to move forward until pressing part 23P abuts on the lower end (other end 13) of suspended part 15 of finger clip part 14D.

By moving gasket 28 forward until it abuts on the upper end inside barrel 11, the movement of plunger 20 relative to medical fluid storage section 10 is stopped (the state shown in FIG. 33). By the stop of the movement of plunger 20, the second administration is completed, and nasal cavity administration container 104 transitions to second administration completion state S26. The amount of stroke of plunger 20 relative to medical fluid storage section 10 defines the second dosage of medical fluid 60. Nasal cavity administration container 104 operates as described above, and the administration of medical fluid 60 by nasal cavity administration container 100 is carried out as described above.

Function and Effect

In nasal cavity administration container 104, as described above, abutting part 25D is provided for plunger 20, and projections 15T are provided for body section 30 (finger clip part 14D). When abutting part 25D of plunger 20 abuts on projections 15T of finger clip part 14D, nasal cavity administration container 104 can easily transition from first administration preparatory state S21 (see FIG. 28) to first administration start state S22 (see FIG. 29). It is noted that abutting part 25D may be provided according to necessity as described above.

In nasal cavity administration container 104, as described above, plunger moving amount regulation member 40D is engaged with body section 30 through first administration preparatory state S21 (see FIG. 28), first administration start state S22 (see FIG. 29S) and first administration completion state S23 (see FIG. 30). The state where plunger moving amount regulation member 40D is engaged with body section 30 can be relieved only in the state where pressing part 23P of plunger 20 abuts on stoppers 42, 43 of plunger moving amount regulation member 40D.

Since plunger moving amount regulation member 40D is not detached from body section 30 until the first administration of medical fluid 60 is completed, nasal cavity administration container 104 can reliably administer an appropriate dosage. Concurrently with the completion of the first administration of medical fluid 60, plunger moving amount regulation member 40D can be easily detached from body section 30 by means of disengaged hook part 46J. Nasal cavity administration container 104 is highly convenient in preparation of the second administration after the first administration is completed.

As described above, in nasal cavity administration container 104, opening 15Q (first fitted part) is provided in body section 30 (specifically, in suspended part 15 of finger clip part 14D). Hook part 46J (second fitted part) is provided for plunger moving amount regulation member 40D. By fitting hook part 46J into opening 15Q, the movement of plunger moving amount regulation member 40D relative to body section 30 is regulated similarly to the above-described second to fourth embodiments. Since plunger moving amount regulation member 40D is fixed relative to body section 30, nasal cavity administration container 104 presents excellent operational stability when pushing plunger 20 into medical fluid storage section 10.

Although embodiments based on the present invention have been described above, the embodiments disclosed herein are illustrative and non-restrictive in every respect. The above embodiments have been described based on the use mode of injecting (sucking) medical fluid 60 into vacant barrel 11, the present invention can also be applied to a so-called pre-filled type that is sold or transferred with barrel 11 previously filled up with medical fluid 60 and is used in that state. Therefore, the technical scope of the present invention is defined by the claims, and is intended to include any modification within the scope and meaning equivalent to the claims.

REFERENCE SIGNS LIST 10 medical fluid storage section; 11 barrel; 11H, 13H, 14H, 14J opening; 11R flange part (first fitted part); 12, 22 end; 12M spray nozzle; 12N nozzle; 13, 23 the other end; 14, 14A, 14B, 14C, 14D finger clip part; 14U, 15U notch; 15 suspended part; 15C recess (first fitted part); 15P projection (first fitted part); 15Q opening (first fitted part); 15T projection; 15V folded portion; 20 plunger; 21 rib; 23P pressing part; 24 leading end; 25, 25D abutting part (second abutting part); 26 constricted part; 27 abutting part (first abutting part); 28 gasket; 29 abutting part; 30 body section; 40, 40A, 40B, 40C, 40D plunger moving amount regulation member; 40M long slot; 40Y rib; 41 grip; 41T end face; 42, 43 stopper; 42E, 43E grasping part; 46 guard part; 46C opening (second fitted part); 46K recess (second fitted part); 46J hook part (second fitted part); 46P projection (second fitted part); 60 medical fluid; 62 air; 100, 101, 102, 103, 104 nasal cavity administration container; AR1, AR2, AR2a, AR3, AR4, AR14D, AR20, AR20C, AR40, AR40A, AR40B, AR40C, AR40D, AR41C arrow; H1, H2 dimension; L1, L2, L3 distance, S11, S21 first administration preparatory state; S12, S22 first administration start state; S13, S23 first administration completion state; S14, S24 second administration preparatory state; S15, S25 second administration start state; S16, S26 second administration completion state.

The invention claimed is:

1. A nasal cavity administration container, comprising:
a body section including a medical fluid storage section, the body section being provided with a spray nozzle on a first end and an opening on a second end opposite the first end;
a plunger to be inserted into said medical fluid storage section from the second end through said opening, said plunger being provided with a pressing part on an end adjacent the second end; and
a plunger moving amount regulation member including a stopper arranged between said pressing part and said opening and being releasably engaged with said body section, wherein
said plunger is pushable into said medical fluid storage section, thereby moving toward the first end until said pressing part abuts on said stopper,
said plunger is further pushable into said medical fluid storage section with said plunger moving amount regulation member detached from said body section,
said plunger moving amount regulation member is completely detachable from said body section while said plunger is inserted into said medical fluid storage section,
said plunger includes ribs having a thin plate shape, the ribs standing up to extend outward perpendicular to a longitudinal axis of said plunger,
said plunger moving amount regulation member has a pair of grasping parts to be engaged with said plunger so as to externally grasp said ribs of said plunger,
a constricted part is provided on said end of said plunger,
a first distance between said pair of grasping parts is provided to be smaller than a second distance between leading ends in the standing direction of said ribs,
the first distance between said pair of grasping parts is provided to be wider than a third distance between leading ends of said constricted part, and
in a state where said pressing part abuts on said stopper, said grasping part is positioned to be opposed to said constricted part, and an engagement of said plunger moving amount regulation member with said plunger is releasable.

2. The nasal cavity administration container according to claim 1, wherein
said plunger has an abutting part located between said stopper and said pressing part in the state where said plunger moving amount regulation member is engaged with said body section,
said plunger is inserted into said medical fluid storage section to cause said abutting part to abut on one of said stopper and said body section, and
said plunger is pushed into said medical fluid storage section, thereby releasing an abutment of said plunger on one of said stopper and said body section.

3. The nasal cavity administration container according to claim 1, wherein
a first fitted part is provided on an outer circumferential surface of said body section,
said plunger moving amount regulation member has a second fitted part to be fitted to said first fitted part in a state where said plunger moving amount regulation member is attached to said body section, and
a movement of said plunger moving amount regulation member attached to said body section relative to said body section is regulated by a fit between said first fitted part and said second fitted part.

4. The nasal cavity administration container according to claim 3, wherein
said plunger has an abutting part located between said stopper and said pressing part in the state where said plunger moving amount regulation member is engaged with said body section,
said plunger is inserted into said medical fluid storage section to cause said abutting part to abut on one of said stopper and said body section, and
said plunger is pushed into said medical fluid storage section, thereby releasing an abutment of said plunger on one of said stopper and said body section.

5. The nasal cavity administration container according to claim 3, wherein said plunger has a first abutting part releasing an engagement between said first fitted part and said second fitted part with said pressing part abutting on said stopper.

6. The nasal cavity administration container according to claim 5, wherein
said plunger has a second abutting part located between said stopper and said pressing part in the state where said plunger moving amount regulation member is engaged with said body section,
said plunger is inserted into said medical fluid storage section to cause said second abutting part to abut on one of said stopper and said body section, and
said plunger is pushed into said medical fluid storage section, thereby releasing an abutment of said plunger on one of said stopper and said body section.

* * * * *